(12) United States Patent
Ye

(10) Patent No.: US 10,950,011 B2
(45) Date of Patent: Mar. 16, 2021

(54) METHOD AND SYSTEM FOR DETERMINING MAGNETIC SUSCEPTIBILITY DISTRIBUTION

(71) Applicant: SHANGHAI UNITED IMAGING HEALTHCARE CO., LTD., Shanghai (CN)

(72) Inventor: Yongquan Ye, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 139 days.

(21) Appl. No.: 16/247,098

(22) Filed: Jan. 14, 2019

(65) Prior Publication Data

US 2019/0318511 A1 Oct. 17, 2019

(30) Foreign Application Priority Data

Apr. 11, 2018 (CN) .......................... 201810323015.X

(51) Int. Cl.
*G06K 9/00* (2006.01)
*G06T 11/00* (2006.01)
*G06K 9/62* (2006.01)

(52) U.S. Cl.
CPC .......... *G06T 11/005* (2013.01); *G06K 9/6202* (2013.01)

(58) Field of Classification Search
CPC .............. G01R 33/243; G01R 33/4824; G01R 33/565; G01R 33/56; A61B 5/4064; A61B 5/055; G06T 11/005; G06K 9/6202
See application file for complete search history.

(56) References Cited

U.S. PATENT DOCUMENTS

| 8,422,756 | B2 | 4/2013 | Haacke et al. |
| 8,693,761 | B2 | 4/2014 | Haake et al. |
| 8,781,197 | B2 | 7/2014 | Wang et al. |
| 8,886,283 | B1 * | 11/2014 | Chen .................. A61B 5/055 600/410 |
| 9,336,611 | B2 | 5/2016 | Bilgic et al. |

(Continued)

OTHER PUBLICATIONS

Tian et al, "Morphology Enabled Dipole Inversion (MEDI) from a Single-Angle Acquisition: Comparison with COSMOS in Human Brain Imaging", Magnetic Resonance in Medicine 66:777-783 (2011) (Year: 2011).*

(Continued)

*Primary Examiner* — Amara Abdi
(74) *Attorney, Agent, or Firm* — Metis IP LLC

(57) ABSTRACT

Systems and methods for determining a distribution map of susceptibility property of an object are provided. The method may include one or more of the following operations. A phase diagram corresponding to a magnetic resonance (MR) signal of the object may be obtained. A preliminary field map may be determined based on the phase diagram. Preliminary error limiting information associated with the preliminary field map may be obtained. A preliminary distribution map of susceptibility property of the object may be determined based on the preliminary field map and the preliminary error limiting information. An iteration process including at least one iteration may be performed to determine a target distribution map of susceptibility property of the object.

20 Claims, 15 Drawing Sheets

(56) References Cited

U.S. PATENT DOCUMENTS

| | | | |
|---|---|---|---|
| 2011/0044524 A1* | 2/2011 | Wang | G01R 33/54 382/131 |
| 2012/0321162 A1 | 12/2012 | Liu et al. | |
| 2013/0188854 A1 | 7/2013 | Bilgic et al. | |
| 2015/0145514 A1* | 5/2015 | Sharma | G01R 33/243 324/309 |
| 2015/0310639 A1* | 10/2015 | Bilgic | A61B 5/4848 382/131 |
| 2015/0323633 A1 | 11/2015 | Cauley et al. | |
| 2018/0059198 A1* | 3/2018 | Shirai | G06T 11/003 |

OTHER PUBLICATIONS

Wei et al, "A method for estimating and removing streaking artifacts in quantitative susceptibility mapping", "2014 Published by Elsevier Inc."), (Year: 2014).*

Liu et al, "quantitative susceptibility mapping: contrast mechanisms and clinical applications", Tomography: Sep. 2015, 1(1): 3-17 (Year: 2015).*

Liu et al, "Morphology enabled dipole inversion for quantitative susceptibility mapping using structural consistency between the magnitude image and the susceptibility map", NeuroImage 59 (2012) 2560-2568, science direct (Year: 2012).*

Jacob Meikeke et al., Quantitative Susceptibility Mapping in Alzheimer's disease using Joint background-field removal and Segmentation-Enhanced Dipole Inversion, in Proceedings of the 24th Annual Meeting of ISMRM, 2016, pp. 1-2 (Year: 2016).*

Ludovic De Rochefort et al., Quantitative MR Susceptibility Mapping Using Piece-Wise Constant Regularized Inversion of the Magnetic Field, Magnetic Resonance in Medicine, 60: 1003-1009, 2008.

Liu, Tian et al., Morphology Enabled Dipole Inversion (MEDI) from a Single-Angle Acquisition: Comparison with COSMOS in Human Brain Imaging, Magnetic Resonance in Medicine, 66: 777-783, 2011.

Liu, Jing et al., Morphology enabled dipole inversion for quantitative susceptibility mapping using structural consistency between the magnitude image and the susceptibility map, NeuroImage, 59(3): 2560-2568, 2012.

Berkin Bilgic et al., Fast Quantitative Susceptibility Mapping with L1-Regularization and Automatic Parameter Selection, Magnetic Resonance in Medicine, 72(5): 1444-1459, 2014.

Li, Wei et al., Quantitative susceptibility mapping of human brain reflects spatial variation in tissue composition, NeuroImage, 55(4): 1645-1656, 2011.

Ferdinand Schweser et al., Quantitative susceptibility mapping for investigating subtle susceptibility variations in the human brain, NeuroImage, 62(3): 2083-2100, 2012.

Bao, Lijun et al., Quantitative Susceptibility Mapping Using Structural Feature Based Collaborative Reconstruction (SFCR) in the Human Brain, IEEE Transactions on Medical Imaging, 35(9): 2040-2050, 2016.

Li, Wei et al., A method for estimating and removing streaking artifacts in quantitative susceptibility mapping, NeuroImage, 108: 111-122, 2015.

Wei, Hongjiang et al., Streaking artifact reduction for quantitative susceptibility mapping of sources with large dynamic range, NMR Biomed., 28(10): 1294-1303, 2015.

E. Mark Haacke et al., Quantitative susceptibility mapping: current status and future directions, Magnetic Resonance Imaging, 33(1): 1-25, 2015.

Liu, Chunlei et al., Quantitative Susceptibility Mapping: Contrast Mechanisms and Clinical Applications, Tomography, 1(1): 3-17, 2015.

Wang, Yi et al., Quantitative Susceptibility Mapping (QSM): Decoding MRI Data for a Tissue Magnetic Biomarker, Magnetic Resonance Medicine, 73(1): 82-101, 2015.

Christian Langkammer et al., Quantitative Susceptibility Mapping: Report From the 2016 Reconstruction Challenge, Magnetic Resonance in Medicine, 79: 1661-1673, 2018.

Jackob Meineke et al., Quantitative Susceptibility Mapping in Alzheimer's Disease using Joint background-field removal and segmentation-Enhanced Dipole Inversion, In Proceedings of the 24th Annual Meeting of ISMRM, 2016, 2 pages.

* cited by examiner

METHOD AND SYSTEM FOR DETERMINING MAGNETIC SUSCEPTIBILITY DISTRIBUTION

CROSS-REFERENCE TO RELATED APPLICATIONS

This application claims priority to Chinese Patent Application No. 201810323015.X, filed on Apr. 11, 2018, the contents of which are hereby incorporated by reference.

TECHNICAL FIELD

This disclosure generally relates to a method and system for magnetic resonance imaging, and more particularly, to a method and system for determining a magnetic susceptibility distribution map of an object.

BACKGROUND

Almost all material can become magnetized in a magnetic field and then display magnetic effects similar to magnets (e.g. generating a local magnetic field around the material). Magnetic resonance imaging (MRI) uses externally imposed magnetic fields (including a main magnet and a gradient magnet) and radio frequency waves to generate images of an object. The object is magnetized in the externally imposed magnetic fields and generates local magnetic fields. The local magnetic fields superimpose with the externally imposed magnetic fields, and may affect the signal of MRI. Susceptibility property (or referred to as magnetic susceptibility or magnetic susceptibility property) is a measure of the extent of a material becomes magnetized in a magnetic field, or in other words, the intensity of a local magnetic field generated by the material (if magnetized). The susceptibility property of an object can be used to derive information such as the content of iron, the degree of calcification, and/or the blood oxygen level in tissue or an organ of the object.

Quantitative Susceptibility Mapping (QSM) is an emerging technique in MRI for determining the susceptibility property of an object. A general process of QSM technology includes obtaining one or more sets of magnetic resonance phase information or phase images, generating a local field map based on the phase information, and determining a distribution map of the magnetic susceptibility based on the local field map and a formulated relationship between the local field map and the distribution map of the magnetic susceptibility. The local field map can be approximated to a convolution of a dipole kernel and the distribution map of the magnetic susceptibility. Accordingly, the distribution map of the magnetic susceptibility can be determined based on the local field map and an inverse dipole kernel. Unlike the dipole kernel, the inverse dipole kernel contains singularity values, thus making the inverse problem mathematically ill-posed and leading to apparent streaking artifacts in the solution results.

The current QSM techniques are facing at least two problems. The first problem is that there may be computational related streaking artifacts in the QSM maps due to the ill-posed nature of the inverse dipole kernel. Superficially, the streaking artifacts occur mainly due to the existence of the singularity values in the inverse dipole kernel. Thus the streaking artifacts can be reduced when the degree of singularity is reduced (which is the basic principle of the truncated k-space QSM methods). However, the truncated k-space QSM method(s) can change the inverse dipole kernel, and may lead to underestimated susceptibility values. And even the artifact is reduced, the remnant streaks usually remains visible in the final distribution maps. The co-localization of a priori information and the susceptibility distribution may reduce the streaking artifacts by adding regularization to the QSM. However, the discrepancy between the a priori information and the actual susceptibility distribution may lead to either over- or under-regularization, affecting the accuracy of the results. Also for tissues or regions with strong susceptibility variance, such as air-tissue boundaries or large bleedings in tissues, relatively strong streaking artifacts may be produced, affecting other regions of interest.

The second problem arises from anatomical a priori information that is involved in solving optimizing QSM as mentioned. The a priori information may provide a reference for the spatial characteristics of the susceptibility distribution (e.g., spatial continuity within tissue, and/or boundaries between different tissues). With such spatial information, one can impose a certain restriction in the form of, e.g., regularization terms (or Bayesian statistics), in solving the ill-posed inverse dipole problem. However, the obtained a priori information may be inaccurate, and the inaccurate a priori information may generate convergence errors in QSM. Usually, the a priori information is estimated by, e.g., the magnitude images of the same scan, or an initial estimate of the susceptibility distribution map. However, there can be non-negligible mismatch between the estimate of the a priori information and the actual spatial continuity of the tissue and/or boundaries between different tissues. Also, the estimate of the a priori information is considered constant during the calculation process of current QSM techniques, hence any mismatch in the a priori information estimation may lead to convergence errors of the calculations.

Therefore, it is desirable to provide a method and system for determining a distribution of susceptibility property of the object with reduced convergence errors and suppressed streaking artifacts.

SUMMARY

According to an aspect of the present disclosure, a method for determining a distribution map of susceptibility property of an object is provided. The method may be implemented on a computing device having at least one storage device storing a set of instructions and at least one processor in communication with the at least one storage device. The method may include obtaining a phase diagram corresponding to a magnetic resonance (MR) signal of the object and determining a preliminary field map based on the phase diagram. The method may further include obtaining preliminary error limiting information associated with the preliminary field map and determining, based on the preliminary field map and the preliminary error limiting information, a preliminary distribution map of susceptibility property of the object. The method may include performing an iteration process including at least one iteration. Each of the at least one iteration may include updating error limiting information in a current iteration based on a distribution map of susceptibility property of the object updated in a preceding iteration; updating the distribution map of susceptibility property of the object in the current iteration based on the error limiting information updated in the current iteration; and performing a comparison based on the updated distribution map in the current iteration and the preliminary field map. The method may further include designating the updated distribution map of susceptibility property of the object as a target distribution map of susceptibility property of the object.

In some embodiments, the performing a comparison based on the updated distribution map in the current iteration and the preliminary field map may include generating an estimated field map based on the updated distribution map of susceptibility property of the object in the current iteration; comparing the estimated field map with the preliminary field map; and determining whether the updated distribution map in the current iteration satisfies a condition based on a result of the comparison between the estimated field map and the preliminary field map.

In some embodiments, the comparing the estimated field map with the preliminary field map may include determining a difference field map between the estimated field map and the preliminary field map; and determining an evaluation value based on the difference field map. The determining whether the updated distribution map in the current iteration satisfies a condition may include comparing the evaluation value with a threshold.

In some embodiments, the error limiting information may include an a priori map, and the obtaining preliminary error limiting information may include determining at least one of a magnitude diagram, a phase diagram, a susceptibility weighted imaging (SWI) map, or a R2* (T2*) map based on the MR signal; and determining a preliminary a priori map based on the at least one of the magnitude diagram, the phase diagram, the susceptibility weighted imaging (SWI) map, or the R2* (T2*) map.

In some embodiments, the error limiting information may include an a priori map, and the updating error limiting information in a current iteration based on the distribution map of susceptibility property of the object updated in a preceding iteration may include determining a feature map in the current iteration based at least in part on the distribution map of susceptibility property of the object updated in the preceding iteration; and updating the a priori map based on the feature map.

In some embodiments, the distribution map of susceptibility property of the object updated in the current iteration may include a plurality of pixels, each pixel of the distribution map of susceptibility property of the object in the current iteration having a pixel value. The feature map may include a plurality of pixels having a one-to-one correspondence with the plurality of pixels of the distribution map of susceptibility property of the object. The determining a feature map in the current iteration based on the distribution map of susceptibility property of the object updated in the preceding iteration may include, for each of the plurality of pixels in the feature map, determining an evaluation value between a pixel value of a first pixel and a pixel value of a second pixel adjacent to the first pixel in the distribution map of susceptibility property of the object in the preceding iteration, and designating the evaluation value as a pixel value of a pixel in the feature map of the current iteration that corresponds to the first pixel in the distribution map of susceptibility property of the object.

In some embodiments, the determining an evaluation value between a pixel value of a first pixel and a pixel value of a second pixel next to the first pixel in the distribution map of susceptibility property of the object in the preceding iteration may include determining the evaluation value between the pixel value of the first pixel and the pixel value of the second pixel next to the first pixel in a reference direction, the reference direction including at least one of an X direction, a Y direction, or a Z direction.

In some embodiments, the error limiting information may include an a priori map. The updating error limiting information in a current iteration based on the distribution map of susceptibility property of the object in a preceding iteration may include determining an a priori field map in the current iteration based on the distribution map of susceptibility property of the object in the preceding iteration, and updating the a priori map in the current iteration based on the a priori field map in the current iteration.

In some embodiments, the determining an a priori field map in the current iteration based on the distribution map of susceptibility property of the object in the preceding iteration may include determining the a priori field map in the current iteration by performing a forward dipole kernel function on the distribution map of susceptibility property of the object in the preceding iteration.

In some embodiments, the error limiting information may include an artifact estimation map. The updating error limiting information in a current iteration based on the distribution map of susceptibility property of the object in a preceding iteration may include generating an estimated field map in the current iteration based on the updated distribution map of susceptibility property of the object in the current iteration, determining a difference field map between the estimated field map in the current iteration and the preliminary field map, and updating the artifact estimation map in the current iteration based on the difference field map.

In some embodiments, the generating an estimated field map in the current iteration based on the updated distribution map of susceptibility property of the object in the current iteration may include generating the estimated field map in the current iteration by performing a partial forward dipole kernel function on the updated distribution map of susceptibility property of the object in the current iteration.

In some embodiments, the updating the distribution map of susceptibility property of the object in the current iteration based on the error limiting information updated in the current iteration may include generating the updated distribution map of susceptibility property of the object in the current iteration by subtracting an updated artifact estimation map in the current iteration from the distribution map of susceptibility property of the object in the preceding iteration; or generating the updated distribution map of susceptibility property of the object in the current iteration by using a regularization term relating to an updated artifact estimation map in the iteration process.

In some embodiments, the error limiting information may include an a priori map and an artifact estimation map. The updating the distribution map of susceptibility property of the object in the current iteration based on the error limiting information updated in the current iteration may include generating the updated distribution map of susceptibility property of the object in the current iteration based on the a priori map in the current iteration, the artifact estimation map in the current iteration and the preliminary field map.

In some embodiments, the iteration process may be performed based on at least one of a conjugate gradient, a preconditioned conjugate gradient, quadratic minimization, or split-Bregman.

In some embodiments, the error limiting information may include an a priori map relating to a spatial smoothness, a spatial gradient, edge information, or a weighted property mask of the distribution map of susceptibility property of the object.

According to another aspect of the present disclosure, a system is provided. The system may include at least one storage and at least one processor configured to communicate with the at least one storage. The at least one storage may include a set of instructions or programs. When the at least one processor executes the set of instructions or programs, the at least one processor may be directed to perform one or more of the following operations. The at least one processor may be directed to obtain a phase diagram corresponding to a magnetic resonance (MR) signal of the object, and determine a preliminary field map based on the phase diagram. The at least one processor may be further directed to obtain preliminary error limiting information associated with the preliminary field map, and determine, based on the preliminary field map and the preliminary error limiting information, a preliminary distribution map of susceptibility property of the object. The at least one processor may be further directed to perform an iteration process including at least one iteration. In each of the at least one iteration, the at least one processor may be further directed to update error limiting information in a current iteration based on a distribution map of susceptibility property of the object updated in a preceding iteration; update the distribution map of susceptibility property of the object in the current iteration based on the error limiting information updated in the current iteration; and perform a comparison based on the updated distribution map in the current iteration and the preliminary field map. The at least one processor may be further directed to designate the updated distribution map of susceptibility property of the object as a target distribution map of susceptibility property of the object.

According to another aspect of the present disclosure, a computer readable medium is provided. The computer readable medium may include executable instructions or programs. When executed by at least one processor, the executable instructions or programs may cause the at least one processor to effectuate a method. The method may include one or more of the following operations. The method may include obtaining a phase diagram corresponding to a magnetic resonance (MR) signal of the object and determining a preliminary field map based on the phase diagram. The method may further include obtaining preliminary error limiting information associated with the preliminary field map and determining, based on the preliminary field map and the preliminary error limiting information, a preliminary distribution map of susceptibility property of the object. The method may include performing an iteration process including at least one iteration. Each of the at least one iteration may include updating error limiting information in a current iteration based on a distribution map of susceptibility property of the object updated in a preceding iteration; updating the distribution map of susceptibility property of the object in the current iteration based on the error limiting information updated in the current iteration; and performing a comparison based on the updated distribution map in the current iteration and the preliminary field map. The method may further include designating the updated distribution map of susceptibility property of the object as a target distribution map of susceptibility property of the object.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
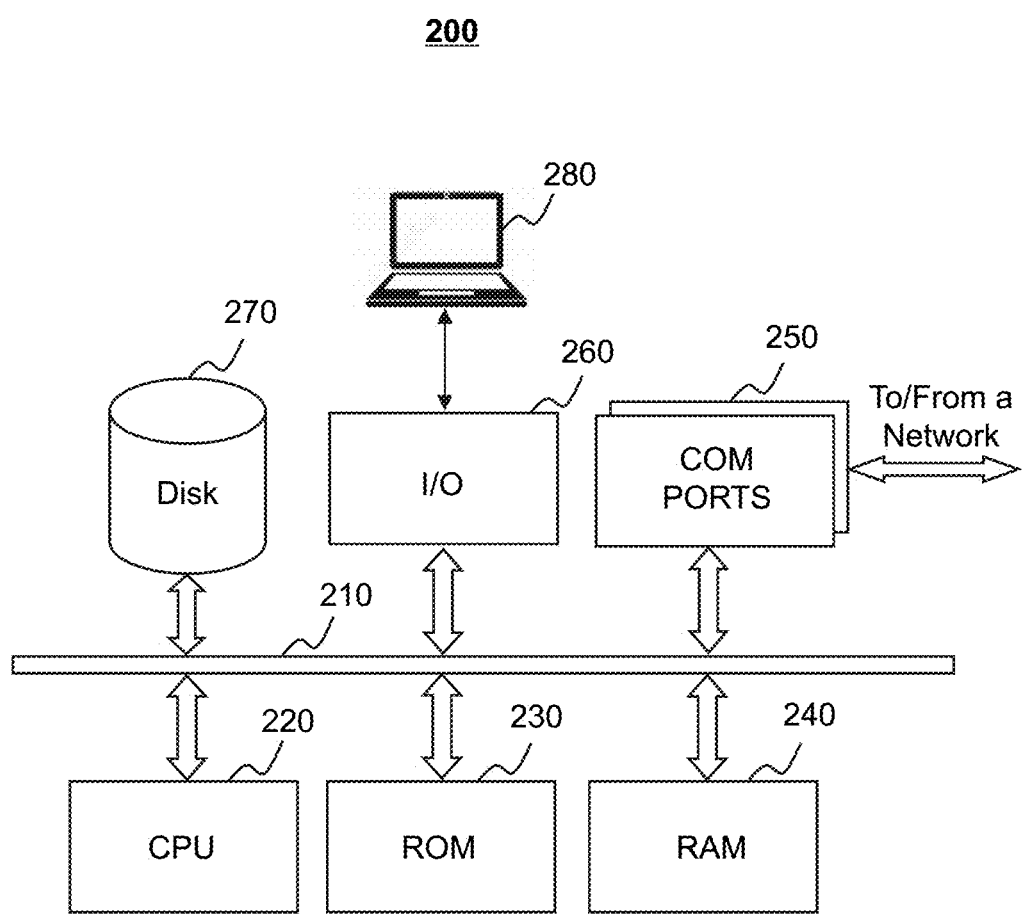
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., CPU 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It should be noted that the terms "magnetic susceptibility map," "susceptibility map," "susceptibility distribution," "susceptibility distribution map," and "distribution map of susceptibility property" may be used interchangeably in the present disclosure to refer to a 3D image or image data of the susceptibility property of a scanned object. It should also be noted that the terms "a priori field map" and "estimated field map" may be used interchangeably in the present disclosure to refer to a 3D image or image data of the magnetic field around an object.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to a method and system for determining a distribution map of susceptibility property of an object. For example, a magnetic resonance (MR) signal of the object may be obtained. The MR signal may include intensity information and frequency information. A magnitude diagram may be generated based on the intensity information, and a phase diagram may be generated based on the frequency information. A preliminary field map may be generated based on the phase diagram. A preliminary error limiting information may be obtained. The preliminary error limiting information may include preliminary a priori information and/or preliminary artifact estimation information. A preliminary distribution map of susceptibility property of the object may be determined based on the preliminary field map and the preliminary error limiting information. An iterative process may be performed. The iterative process may include a plurality of iterations. In each iteration, the error limiting information and the distribution map of susceptibility property may be updated. After the updating of the error limiting information and the distribution map of susceptibility property in each iteration, a difference field map may be constructed based on the updated distribution map of susceptibility property and the preliminary field map. If an evaluation value related to the difference field map is less than a threshold, the iterative process may terminate, and the updated distribution map of susceptibility property may be designated as a target distribution map of susceptibility property of the object.

If the error limiting information includes a prior information, in the iterative process for updating the distribution map of susceptibility property, the a prior information can be dynamically extracted and updated based on the intermediate distribution map of susceptibility property, and the updated a prior information may be applied to the updating of the distribution map of susceptibility property, thereby making the a prior information approach the real spatial characteristics of the susceptibility distribution, and accelerating the convergence speed of the iterative process and improve the accuracy of the results (i.e., the distribution map of susceptibility property).

If the error limiting information includes artifact estimation information, in the iterative process, the artifact estimation information is dynamically updated based on intermediate distribution map of susceptibility property, and the updated artifact estimation information may be used as a regularization term and applied to the iterative process (or the updated artifact estimation information may be removed directly from the distribution map of susceptibility property), thereby reducing the artifact intensity of the distribution map of susceptibility property to a negligible level without affecting other calculation procedures, and ensuring the accuracy of the results (i.e., the distribution map of susceptibility property).

Figure 1:
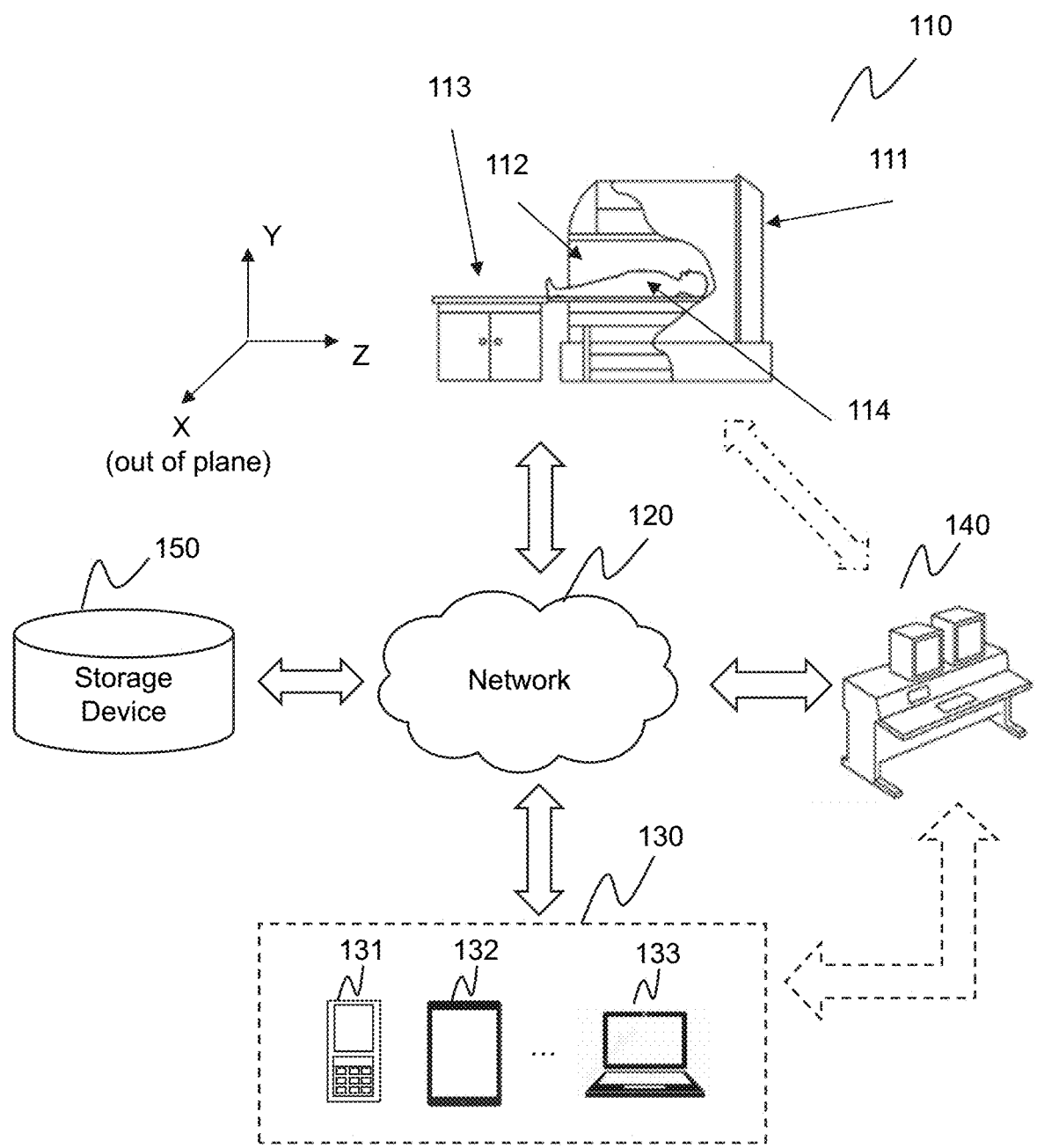
FIG. 1 is a schematic diagram illustrating an exemplary imaging system according to some embodiments of the present disclosure.

FIG. 1 is a schematic diagram illustrating an exemplary imaging system according to some embodiments of the present disclosure. As shown in FIG. 1, the imaging system 100 may include a scanner 110, a network 120, one or more terminals 130, a processing device 140, and a storage device 150. All the components in the imaging system 100 may be interconnected via the network 120.

The scanner 110 may scan an object 114 and generate scanned data relating to the object 114. The object 114 may be biological or non-biological. Merely by way of example, the object 114 may include a patient, an organ, a tissue, a specimen, a man-made object, a phantom, etc. In some embodiments, the scanner 110 may be a single-modality medical imaging device, such as, an MRI device, a PET device, a SPECT device, a CT device, or the like, or a multi-modality medical imaging device, such as, a PET-MRI device, a SPECT-MRI device, or a PET-CT device. Taking an MRI scanner (e.g., the MRI device, the PER-MRI device, the SPECT-MRI device) as an example, the scanner 110 may include a gantry 111 and a scanning bed 113. The scanner 110 may also include a main magnet, a gradient magnet, a pulse controller, a gradient signal generator, a radiofrequency (RF) pulse generator, an RF signal receiver (or collectively referred to as an RF signal transceiver), and coils (not shown in FIG. 1). The scanner 110 may obtain information related to the object 114 by scanning the object 114. More particularly, certain atomic nuclei (e.g., hydrogen-1, carbon-13, oxygen-17, etc.) may absorb and emit RF energy when being placed in the main magnetic and the gradient magnetic fields. The emitted RF energy exists as RF signals and is received by the scanner 110. The scanner 110 may obtain information for reconstructing a distribution of the atomic nuclei inside the object 14 based on the RF signals as an MRI image.

The main magnet may be placed in the gantry 111 of the scanner 110. The main magnet may be configured to generate a (substantially) uniform main magnetic field. The strength of the main magnetic field may be, e.g., 0.2 Tesla, 0.5 Tesla, 1.0 Tesla, 1.5 Tesla, 3.0 Tesla, etc. In some embodiments, the main magnet may be a superconducting coil. Alternatively, the main magnet may be a permanent magnet.

The scanning bed 113 may support the object 114 during a scan. For example, the object 114 may be supported and/or delivered to the detecting region 112 of the gantry 111 by the scanning bed 113. The detecting region 112 may be a region that the magnetic field distribution of the main magnetic field is relatively uniform, and to which, the RF signal is transmitted.

Merely by way of example, a spatial coordinate system (i.e., a coordinate system of the scanner 110) may be described with reference to the gantry 111 of the scanner 110. For example, a Z axis may be the direction along the axis of the gantry, an X axis and a Y axis may be the directions perpendicular to the Z axis. As illustrated in FIG. 1, the X axis may be along the horizontal direction, and the Y axis may be along the vertical direction. The long-axis direction of the object 114 may coincide with the direction of the Z axis, and the scanning bed 113 may move in the direction of the Z axis.

The pulse controller may be configured to control the generation of RF signals. For example, the pulse controller may control the RF pulse generator and the gradient signal generator. In some embodiments, the pulse controller may control the RF pulse generator to generate an RF pulse. The RF pulse may be amplified by an amplifier. In some embodiments, the pulse controller may control the gradient signal generator to generate gradient signals. The pulse controller may receive information from or send information to the scanner 110, the processing device 140, and/or a terminal 130. According to some embodiments of the present disclosure, the pulse controller may receive a command from a user via the terminal 130 or a display (e.g., display 450) of the processing device 140 and control components of the scanner 110 (e.g., the RF pulse generator) accordingly to start a scan.

The RF pulse generator may generate an RF pulse. In some embodiments, the RF pulse generator may generate the RF pulse based on an instruction from the pulse controller. The RF pulse may be amplified by an amplifier. A switch may be configured to control the emission of the amplified RF pulse. For example, the amplified RF pulse may be emitted by the coils when the switch is on. The emitted RF pulse may excite the atomic nuclei in the object 114. The object 114 may generate a corresponding RF signal when the RF excitation is removed. The coils may transmit RF signals to or receive RF signals from the object 114. For example, the coils may transmit the amplified RF pulse to the object 114. As another example, the coils may receive the RF signals emitted from the object 114. In some embodiments, the coils may include a plurality of RF receiving channels. The plurality of RF receiving channels may transmit RF signals received from the object 114 to the RF signal receiver. The RF signal receiver may be configured to receive RF signals. The RF signal receiver may receive RF signals from the coils. In some embodiments, the coils may include a volume coil configured to transmit RF signals to or receive RF signals from the entire body of the object 114 and/or a local coil configured to transmit RF signals to or receive RF signals from a portion of the object 114.

The gradient signal generator may generate gradient signals. In some embodiments, the gradient signal generator may generate gradient signals based on an instruction from the pulse controller. The gradient signals may include three orthogonal signals. In some embodiments, the three orthogonal signals may be a first gradient signal along the X direction, a second gradient signal along the Y direction, and a third gradient signal along the Z direction. The gradient signals may facilitate to locate the atomic nuclei.

The gradient magnet may be configured to spatially encode RF signals (e.g., an RF pulse generated by the RF pulse generator). The gradient magnet may generate a magnetic field with a strength less than that of the main magnetic field. For example, the gradient magnet may generate a gradient magnetic field in the detecting region 112.

The network 120 may include any suitable network that can facilitate the exchange of information and/or data for the imaging system 100. In some embodiments, one or more components of the imaging system 100 (e.g., the scanner 110, the terminal 130, the processing device 140, the storage device 150, etc.) may communicate information and/or data with one or more other components of the imaging system 100 via the network 120. For example, the processing device 140 may obtain image data from the scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. The processing device 140 may be configured to process the MR signals received from the RF signal receiver and/or generate one or more MR images based on the MR signals. The processing device 140 may process the received MR signals to generate and/or update a magnitude diagram, a phase diagram, a susceptibility map, an R2* (T2*) map, a susceptibility weighted imaging (SWI) map, or the like, or a combination thereof. In some embodiments, the processing device 140 may perform an iterative process for updating the distribution map of susceptibility property and error limiting information.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the imaging system 100 (e.g., the processing device 140, the terminal 130, etc.). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal 130, etc.). In some embodiments, the storage device 150 may be part of the processing device 140.

FIG. 2 is a schematic diagram illustrating exemplary hardware and software components of a computing device according to some embodiments of the present disclosure. The computing device 200 may be a general purpose computer or a special purpose computer; both may be used to implement an imaging system 100 of the present disclosure. In some embodiments, the processing device 140 may be implemented on the computing device 200, via its hardware, software program, firmware, or a combination thereof. Although only one such computer is shown, for convenience, the computer functions as described herein may be implemented in a distributed manner on a number of similar platforms, to distribute the processing load.

The computing device 200, for example, may include COM ports 250 connected to and from a network connected thereto to facilitate data communications. The computing device 200 may also include a central processing unit (CPU) 220, in the form of one or more processors, for executing program instructions. The exemplary computer platform may include an internal communication bus 210, program storage and data storage of different forms, for example, a disk 270, and a read-only memory (ROM) 230, or a random access memory (RAM) 240, for various data files to be processed and/or transmitted by the computer. The exemplary computer platform may also include program instructions stored in the ROM 230, RAM 240, and/or another type of non-transitory storage medium to be executed by the CPU 220. The methods and/or processes of the present disclosure may be implemented as the program instructions. The computing device 200 also includes an I/O component 260, supporting input/output between the computer and other components therein such as user interface elements 280. The computing device 200 may also receive programming and data via network communications.

The computing device 200 may also include a hard disk controller communicated with a hard disk, a keypad/keyboard controller communicated with a keypad/keyboard, a serial interface controller communicated with a serial peripheral equipment, a parallel interface controller communicated with a parallel peripheral equipment, a display controller communicated with a display, or the like, or any combination thereof.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the CPU and/or processor of the computing device 200 executes both operation A and operation B (e.g., the updating of distribution map of susceptibility property of the object and the updating of error limiting information), it should be understood that operation A and operation B may also be performed by two or more different CPUs and/or processors jointly or separately in the computing device 200 (e.g., a first processor updates the distribution map of susceptibility property of the object and a second processor updates the error limiting information, or the first and second processors jointly update the distribution map of susceptibility property of the object and the error limiting information).

Figure 3:
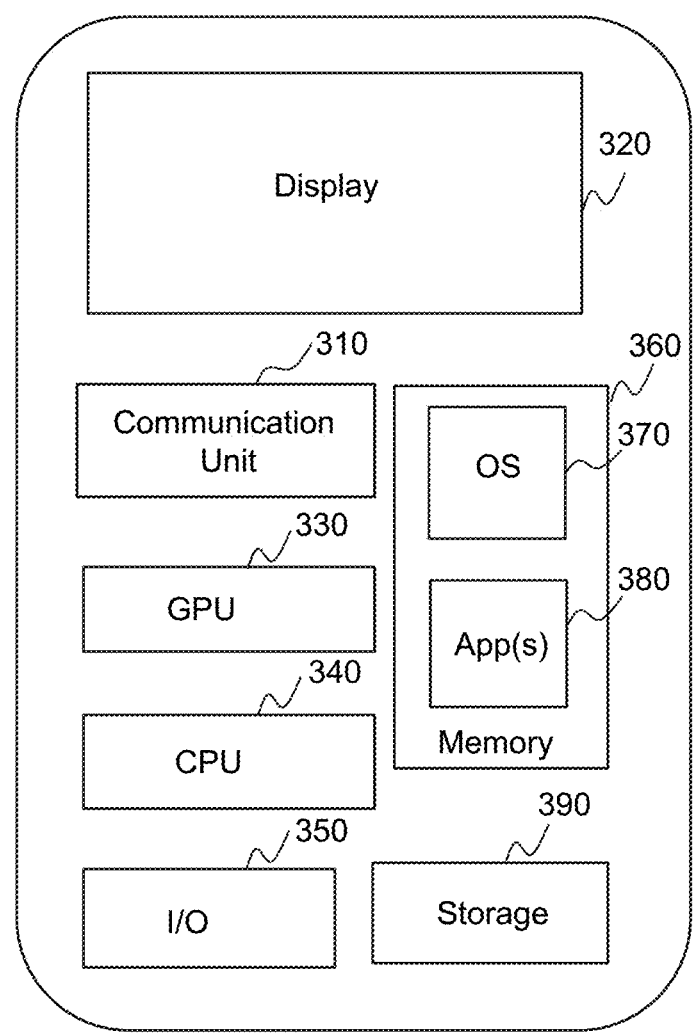
FIG. 3 is a schematic diagram illustrating exemplary hardware and/or software components of an exemplary mobile device that is configured to implement a specific system disclosed in the present disclosure.

FIG. 3 is a schematic diagram illustrating exemplary hardware and/or software components of an exemplary mobile device that is configured to implement a specific system disclosed in the present disclosure. As illustrated in FIG. 3, the mobile device 300 may include a communication unit 310, a display 320, a graphics processing unit (GPU) 330, a CPU 340, an I/O 350, a storage 390, and a memory 360. In some embodiments, any other suitable component, including but not limited to a system bus or a controller (not shown), may also be included in the mobile device 300. In some embodiments, a mobile operating system 370 (e.g., IOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120. In some embodiments, a user may input parameters to the imaging system 100, via the mobile device 300.

In order to implement various modules, units and their functions described above, a computer hardware platform may be used as hardware platforms of one or more elements (e.g., the processing device 140 and/or other components of the imaging system 100 described in FIG. 1). Since these hardware elements, operating systems and program languages are common; it may be assumed that persons skilled in the art may be familiar with these techniques and they may be able to provide information required in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computer device. Thus, extra explanations are not described for the Figures.

Figure 4:
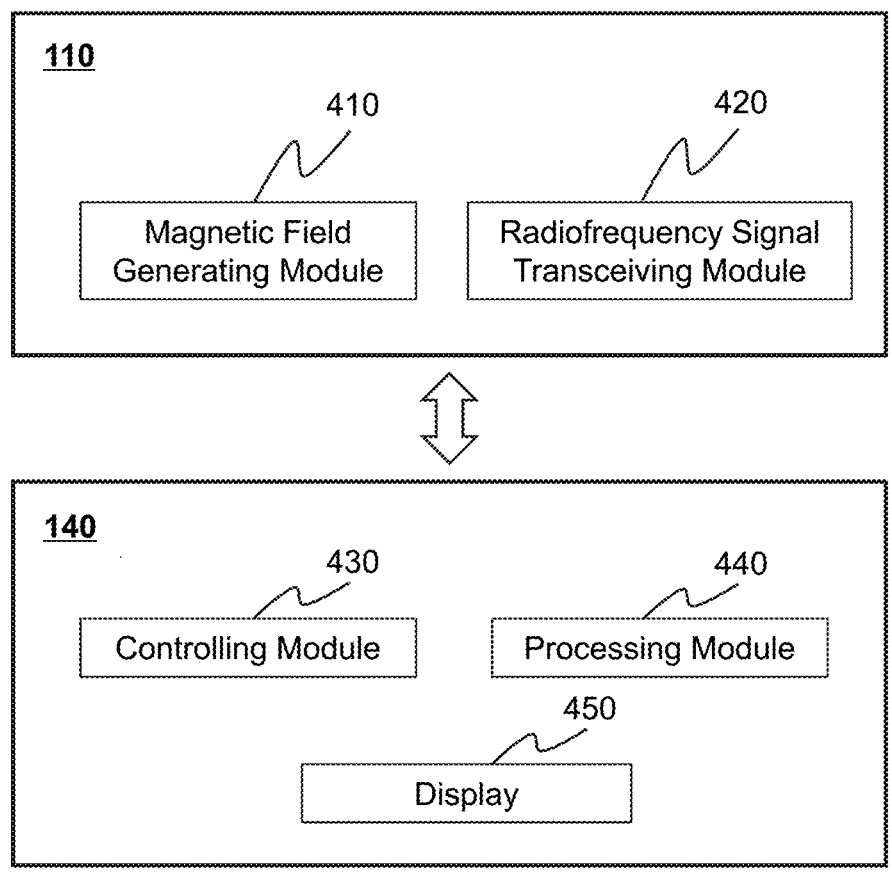
FIG. 4 is a schematic diagram illustrating an exemplary scanner and an exemplary processing device according to some embodiments of the present disclosure.

FIG. 4 is a schematic diagram illustrating an exemplary scanner and an exemplary processing device according to some embodiments of the present disclosure. As shown in FIG. 4, the scanner 110 may include a magnetic field generating module 410 and a radiofrequency signal transceiving module 420. The processing device 140 may include a controlling module 430, a processing module 440, and a display 450. In some embodiments, the scanner 110 may communicate with the processing device 140 via cables. Alternatively or additionally, the scanner 110 may communicate with the processing device 140 via the network 120. In some embodiments, the scanner 110 and the processing device 140 may be integrated into a single component that performs either or both of their functions.

In some embodiments, the scanner 110 may perform a scan on an object (e.g., the object 114) to obtain/acquire magnetic resonance (MR) signals of the object's target site (or region of interest (ROI)). In some embodiments, the scan may be a normal MRI scan on the object (e.g., with normal settings and/or parameters) for generating an MR image of the object or a pre-scan of a phantom for calibrating the imaging system 100.

The magnetic field generating module 410 may include a main magnetic field generator and/or a gradient magnetic field generator. The main magnetic field generator may generate a static magnetic field $B_0$ during the scan. The main magnetic field generator may be of various types including, for example, a permanent magnet, a superconductive magnet, a resistive electromagnet, or the like, or a combination thereof. The gradient magnetic field generator may generate magnetic field gradients Gx, Gy, and Gz in the directions of "X," "Y," and "Z," respectively. As used herein, the X, Y, and Z directions may represent the directions along the X, Y, and Z axes in a coordinate system associated with the scanner 110. Similar to FIG. 1, the X and Z axes may be in a horizontal plane, the X and Y axes may be in a vertical plane, and the Z axis may be along the axis of rotation of the gantry. In some embodiments, the X axis, the Y axis, and the Z axis may be specified by the gradient magnetic field generator (e.g., a gradient coil in a gradient magnetic field generator). The gradient magnetic field generator may encode and/or read spatial information (e.g., X, Y, Z coordinates) of an object or a portion thereof located within the scanner 110. In some embodiments, the gradient magnetic field generator may generate one or more gradient magnetic fields, each of which is in a particular direction during the scan. Merely by way of example, the gradient magnetic field generator may generate a first gradient magnetic field along the X axis, a second gradient magnetic field along the Y axis, and a third gradient magnetic field along the Z axis. In some embodiments, the gradient magnetic fields along the X axis, the Y axis, and/or the Z axis may correspond to different encoding/reading directions in k-space (e.g., the direction of the Kx axis, the direction of the Ky axis, the direction of the Kz axis, or any other directions).

The radiofrequency signal transceiving module 420 may include an RF transmitting coil and/or an RF receiving coil. The RF transmitting coil may transmit RF signals to the object and the RF receiving coil may receive RF signals from the object. In some embodiments, the functionality, size, type, geometry, location, amount, and/or magnitude of the magnetic field generating module 410 and/or the radiofrequency signal transceiving module 420 may be changed according to one or more specific requirements in different scenarios. For example, RF coils may be classified into volume coils and local coils depending on differences in, e.g., their function, size, or the like, or a combination thereof. Exemplary volume coils may include a birdcage coil, a transverse electromagnetic coil, a surface coil, a saddle coil, or the like, or a combination thereof. Exemplary local coils may include a birdcage coil, a solenoid coil, a saddle coil, a flexible coil, or the like, or a combination thereof. In some embodiments, the magnetic field generating module 410 and the radiofrequency signal transceiving module 420 may be configured to surround the object to form a tunnel-type MRI scanner (e.g., a closed-cell MRI scanner, such as the scanner 110 shown in FIG. 1) or an open MRI scanner.

The controlling module 430 may control the magnetic field generating module 410 and/or the radiofrequency signal transceiving module 420 of the scanner 110, the processing module 440, and/or the display 450 of the processing device 140, and/or other components of the imaging system 100. For example, the controlling module 430 may control the strength and direction of the gradient magnetic fields generated by the gradient magnetic field generator. As another example, the controlling module 430 may receive or transmit information from/to the scanner 110, the processing module 440, and/or the display 450. In some embodiments, the controlling module 430 may receive a command (e.g., provided by a user) from the display 450, and operate the magnetic field generating module 410 and/or the radiofrequency signal transceiving module 420 according to the received command to obtain an image of the object. Merely by way of example, the command may relate to an imaging application (e.g., selected by the user), which may include but is not limited to susceptibility weighted imaging (SWI), or quantitative susceptibility mapping (QSM), or the like.

The processing module 440 may be configured to process various kinds of information received from different modules. In some embodiments, the processing module 440 may include a central processing unit (CPU), an application specific integrated circuit (ASIC), an application-specific instruction-set processor (ASIP), a graphics processing unit (GPU), a physics processing unit (PPU), a microcontroller, a digital signal processor (DSP), a field programmable gate array (FPGA), an advanced RISC machine (ARM), or the like, or a combination thereof. The processing module 440 may process the MR signals received from the radiofrequency signal transceiving module 420 and generate one or more MR images based on the MR signals. The processing module 440 may deliver the images to the display 450. In some embodiments, the processing module 440 may process data inputted by the user or operator via the display 450 and transform the data into specific commands and transmit the commands to the controlling module 430. In some embodiments, the processing module 440 may perform the processes as illustrated in FIG. 6 through FIG. 11 to process the received magnetic resonance signals to generate and/or update a magnitude diagram, a phase diagram, a susceptibility map, an R2* (T2*) map, an SWI map, or the like, or a combination thereof.

The display 450 may be configured to display output information. In some embodiments, an input device may be configured to allow a user to provide input. In some embodiments, the input device may be implemented on or operably connected to the display 450. For instance, the display 450 may be a touch screen that allows input and display. The input information and/or output information may include programs, software, algorithms, data, texts, numbers, images, sounds, or the like, or any combination thereof. For example, the user or operator may enter initial MR parameters or settings to initiate a scan. In some embodiments, the controlling module 430, the processing module 440, and/or the display 450 may be integrated into an image generator (e.g., an independent image generator, the terminals 130). The user may set parameters for the MR scan, control the imaging protocol, view the images produced by the image generator on a display thereof. In some embodiments, the display 450 may be a CRT display or an LCD. The display 450 may display an MR signal, a magnitude diagram, a phase diagram, a susceptibility map, an R2* (T2*) map, an SWI map, or the like, or a combination thereof.

Figure 5:
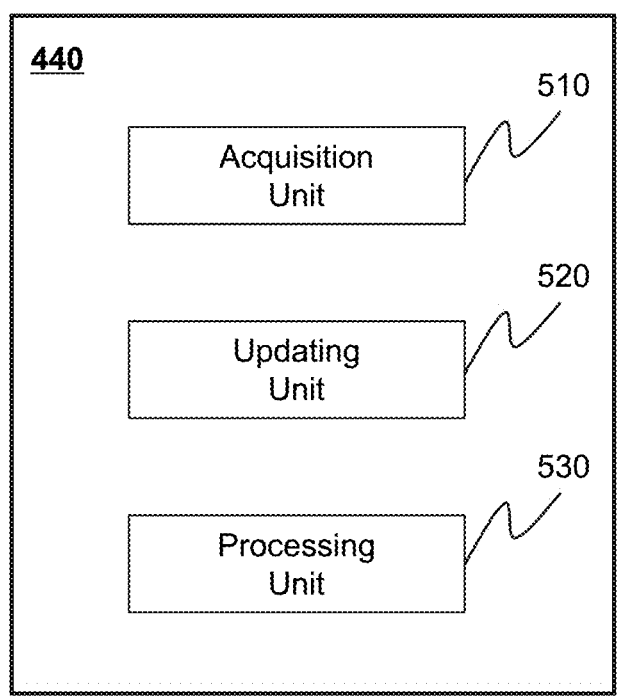
FIG. 5 is a schematic diagram illustrating an exemplary processing module according to some embodiments of the present disclosure.

FIG. 5 is a schematic diagram illustrating an exemplary processing module according to some embodiments of the present disclosure. As shown in FIG. 5, the processing module 440 may include an acquisition unit 510, an updating unit 520, and a processing unit 530.

The acquisition unit 510 may be configured to obtain a preliminary distribution map of susceptibility property of the object based on the preliminary field map and the preliminary error limiting information. Specifically, the preliminary distribution map of susceptibility property of the object may be obtained based on the preliminary field map and at least one of the preliminary a priori information or the preliminary artifact estimation information. In some embodiments, the acquisition unit 510 may receive the MR signals acquired by the scanner 110 and determine the preliminary field map based on the MR signals of the target site of the object. In some embodiments, the acquisition unit 510 may obtain at least one of a magnitude diagram, a phase diagram, an SWI map, or an R2* (T2*) map of the object. The acquisition unit 510 may determine the preliminary a priori information based on the at least one of the magnitude diagram, the phase diagram, the SWI map, or the R2* (T2*) map. The preliminary a priori information may include a spatial smoothness of the susceptibility distribution, a spatial gradient of the susceptibility distribution, edge information of the susceptibility distribution, a weighted property mask, or the like, or any combination thereof.

The updating unit 520 may be configured to perform an iterative process for updating the distribution map of susceptibility property and/or the error limiting information. The iterative process may include a plurality of iterations. In some embodiments, in each iteration, the error limiting information in the current iteration may be updated based on the distribution map of susceptibility property in the preceding iteration, and the distribution map of susceptibility property in the current iteration may be updated based on the error limiting information updated in the current iteration. The error limiting information may include the a priori information and/or the remnant streaking artifact estimation information corresponding to the preliminary field map. For example, the updating unit 520 may, in each iteration, update the a priori information, and determine the distribution map of susceptibility property based on the updated a priori information. As another example, the updating unit 520 may, in each iteration, update the remnant streaking artifact estimation information corresponding to the field map, and determine the distribution map of susceptibility property based on the updated remnant radiation streaking artifacts corresponding to the field map. As a further example, the updating unit 520 may, in each iteration, update both the a priori information and the remnant streaking artifact estimation information, either in sequence or simultaneously, and determine the distribution map of susceptibility property based on the updated a priori information and the updated remnant streaking artifact estimation information.

The processing unit 530 may obtain the updated distribution map of susceptibility property from the updating unit 520. The iterative process may terminate when a termination condition is satisfied. For instance, the termination condition may be that the evaluation value between the preliminary field map and a field map corresponding to the updated distribution map of susceptibility property (e.g., a field map generated by performing a forward dipole kernel function on the updated distribution map of susceptibility property) is less than a threshold when the iterative process terminates. The processing unit 530 may output the updated distribution map of susceptibility property as a target distribution map of susceptibility property of the object.

Figure 6:
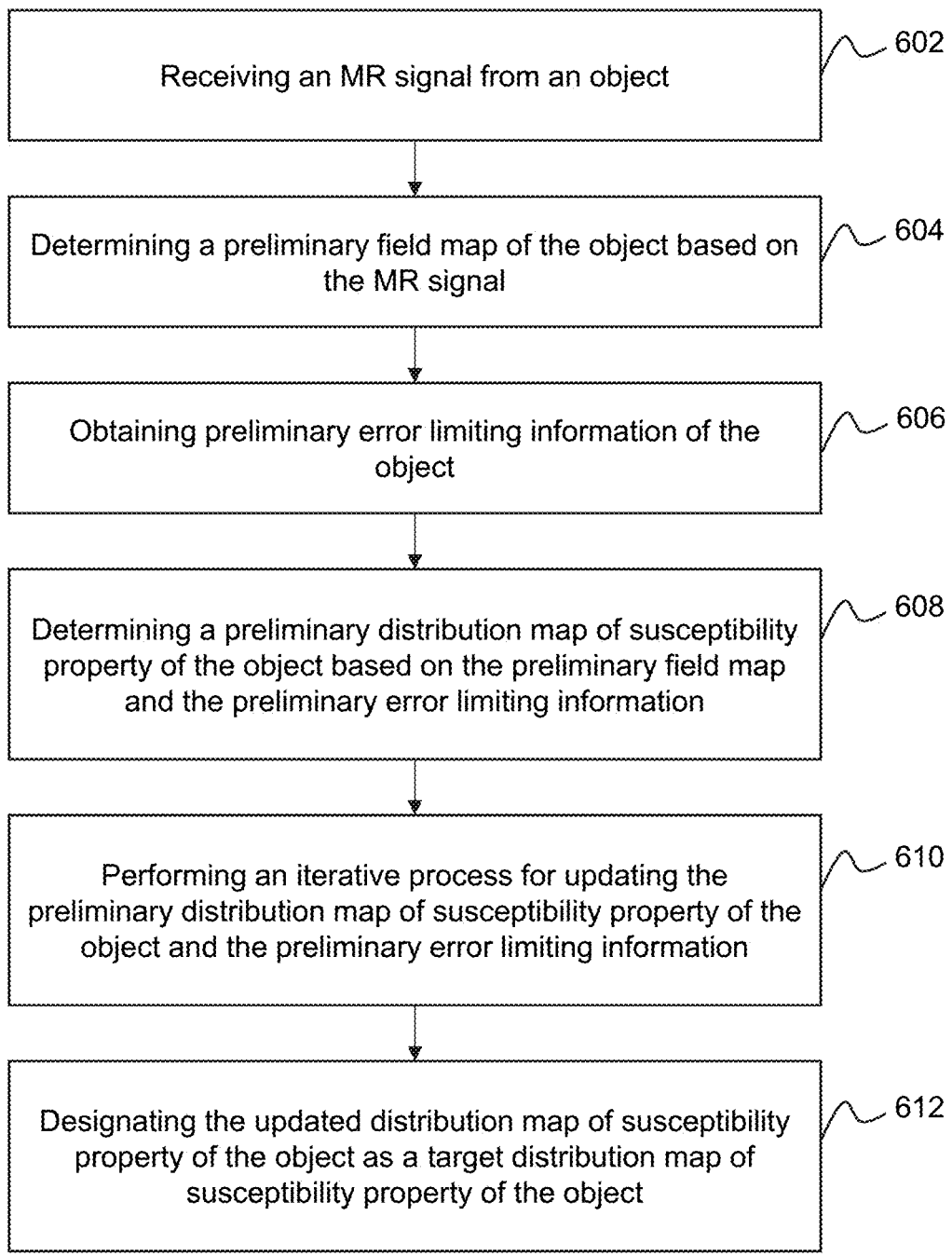
FIG. 6 is a flowchart of an exemplary process for determining a target distribution map of susceptibility property of an object according to some embodiments of the present disclosure.

FIG. 6 is a flowchart of an exemplary process for determining a target distribution map of susceptibility property of an object according to some embodiments of the present disclosure. The process 600 may be executed by the processing device 140. For example, the process 600 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 600.

In 602, the acquisition unit 510 may receive a magnetic resonance (MR) signal from an object (e.g., the object 114). In some embodiments, the object may include a patient, a tissue or organ of a patient, a substance, a specimen, or the like, or any combination thereof. For example, the object may include the head, the chest, the lung, the pleura, the mediastinum, the abdomen, the large intestine, the small intestine, the bladder, the gallbladder, the chest, the pelvic cavity, the backbone, the limb(s), the skeleton, the blood vessel(s), etc., of a patient. In some embodiments, the object or a region of interest (ROI, also referred to as target site) of the object may be excited by an RF signal. When the object or an ROI of the object relaxes, a spin signal or spin echo may be emitted by the object or the ROI of the object. The spin signal or spin echo may be received by the imaging system 100. The spin signal may be phase encoded to form a magnetic resonance (MR) signal.

In 604, the processing unit 530 may determine a preliminary field map of the object based on the MR signal. In some embodiments, phase information of the MR signal may be extracted to generate the preliminary field map of the object. More descriptions regarding the generation of the preliminary field map of the object may be found in, e.g., operations 704 and 706 in FIG. 7 and the descriptions thereof.

In 606, the acquisition unit 510 may obtain preliminary error limiting information of the object. The preliminary error limiting information may include but not limited to a priori information and artifact estimation information.

The a priori information may provide features on the spatial distribution of susceptibility of the object, such as the continuity of distribution within the same tissue, the boundaries between different tissues, etc. For example, the a priori information may include spatial smoothness of the susceptibility distribution of the object, a spatial gradient of the susceptibility distribution of the object, edge information of the susceptibility distribution of the object, a weighted property mask, or the like, or any combination thereof, corresponding to the target site of the object. The a priori information may be obtained from a magnitude map, a phase map, a magnetic susceptibility map, an R2* (T2*) map, or a susceptibility weighted imaging (SWI) map of the object. More descriptions regarding the generation of the preliminary a priori information may be found in, e.g., operations 708, 710 and 712 in FIG. 7 and the descriptions thereof.

The artifact estimation information may include radial streaking artifacts. Due to the ill-posed nature of the inverse dipole problem (e.g., singularity values in the inverse dipole kernel functions), computationally relevant radial streaking artifacts are generated during QSM. Removing the remnant streaking artifacts in the susceptibility map may effectively reduce the intensity of the artifacts and improve the accuracy of the susceptibility map. In some embodiments, preliminary artifact estimation information may be generated based on an estimation. In a case that a preliminary distribution map of susceptibility property of the object is known (e.g., obtained based on the preliminary field map and the a priori information), the preliminary artifact estimation information may be obtained based on a difference map between the preliminary field map and a field map corresponding to the preliminary distribution map of susceptibility property (e.g., an estimated field map, a field map generated by performing a forward dipole kernel function on the preliminary distribution map of susceptibility property).

In 608, the processing unit 530 may determine a preliminary distribution map of susceptibility property of the object based on the preliminary field map and the preliminary error limiting information. Specifically, the preliminary distribution map of susceptibility property of the object may be obtained based on the preliminary field map and at least one of the preliminary a priori information and the preliminary artifact estimation information.

In some embodiments, the preliminary distribution map of susceptibility property of the object may be determined based on Formula (1) as illustrated below:

$$\mathrm{argmin}_{\chi} \|F^{-1}DF\chi - \phi\|_2^2 + \alpha\|P\nabla\chi\|_1 + \beta\|F^{-1}D'F\Delta\phi\|_2^2, \quad (1)$$

where the first part, $\|F^{-1}DF\chi - \phi\|_2^2$, is a basic quadratic minimization of a conversion function between a field map and a susceptibility distribution. In the first part, F and $F^{-1}$ denote Fourier and inverse Fourier operators, respectively, D denotes the forward dipole kernel, $\chi$ denotes the susceptibility distribution, and $\phi$ denotes the field distribution (i.e., the field map). In operation 608, $\chi$ denotes the preliminary distribution map of susceptibility property of the object, and $\phi$ denotes the preliminary field map.

The second part, $\alpha \|P\nabla\Delta\chi\|_1$, is the L1 norm of gradients in all three dimensions of the a priori information. In the second part, $\alpha$ denotes a regularization factor that balances data consistency and spatial smoothness, P denotes a (weighted) property mask that is dynamically extracted from the initial or intermediate $\chi$ during an iterative optimization process, and $\nabla$ denotes a gradient operator. The second part indicates a dynamic updating of the a priori information and/or the use of dynamically updated a priori information. In operation 608, P denotes the preliminary a priori information (e.g., a preliminary property mask). In some embodiments, the property mask may be an image including a plurality of pixels whose values are, e.g., zeros and ones. For instance, values of pixels in a smooth region (e.g., a region inside or outside a type of tissue of the object that have a relatively low gradient variance) may be zero, while values of pixels near boundaries (e.g., boundaries of different tissues, boundaries of different portions of a same tissue) having a relatively high gradient variance may be one. For example, a smooth region inside or outside the liver of the object may have a homogeneous structure, and the gradient variance of the smooth region may be relatively low. As another example, the boundary of the liver of the object may be relatively sharp to differentiate the region inside the liver from that outside the liver, the gradients of the pixels near the boundary may have a large saltation, and then the gradient variance may be relatively high. In some embodiments, the values of pixels may be any value between zero and one. For example, the above-mentioned pixels inside or outside a type of tissue with a relatively low gradient variance may have any value between zero and one (e.g., 0.01, 0.1, 0.3), and the above-mentioned pixels near a boundary between the region inside the tissue and that outside the tissue may be any number between zero and one (e.g., 0.99, 0.9, 0.7). In some embodiments, the values of pixels in the property mask P may be any positive number (even greater than 1).

The third part, $\beta \|F^{-1}D'F\Delta\phi\|_2^2$, is the L2 norm of the estimation of the remnant streaking artifact. In the third part, $\beta$ denotes a scaling factor that adjusts the weighting of the remnant streaking artifact regularization, and D' denotes a partial forward dipole kernel. D' may include only the parts in the dipole kernel that include or are close to the singularities. In some embodiments, the partial forward dipole kernel D' may be obtained by a threshold calculation based on D (e.g., $D'=D\cdot(|D|<\text{thresh})$). $\Delta\phi$ in the third part denotes the difference (also referred to as a difference field map) between an intermediate (or estimated) field map (calculated from the preliminary distribution map of susceptibility property or an intermediate $\chi$ map using the forward dipole kernel) and the preliminary field map. The third part indicates a dynamic estimation of streaking artifact and mitigation of the streaking artifact, and the use of dynamically updated streaking artifact. In operation 608, $\Delta\phi$ denotes the difference between the preliminary field map and the estimated field map corresponding to the preliminary distribution map of susceptibility property.

Formula (1) describes an optimization process, e.g., seeking for a value $\chi$ to make the value of the whole Formula (1) minimum or less than a threshold. Formula (1) may be solved by any kinds of numeric optimization techniques, such as a conjugate gradient, a preconditioned conjugate gradient, quadratic minimization, split-Bregman, or the like, or any combination thereof.

It should be noted that Formula (1) is only an exemplary way of obtaining a preliminary distribution map of susceptibility property. However, Formula (1) may be used to update the distribution map of susceptibility property and the error limiting information. Other ways of obtaining the preliminary distribution map of susceptibility property are also applicable and within the scope of the present disclosure. Also, terms and iteration forms in Formula (1) may be modified or omitted. New terms or iteration forms may be introduced to Formula (1). Such modifications, deletions and/or variations are within the protection scope of the present disclosure.

In 610, the updating unit 520 may perform an iterative process for updating the preliminary distribution map of susceptibility property of the object and the preliminary error limiting information. In some embodiments, the iterative process may include at least one iteration. In some embodiments, the iterative process may include a plurality of iterations. In each of the plurality of iterations, the error limiting information in the current iteration may be updated based on the distribution map of susceptibility property in the preceding iteration; the distribution map of susceptibility property in the current iteration may be updated based on the error limiting information updated in the current iteration. Merely by way of example, the preliminary distribution map of susceptibility property and the preliminary error limiting information may be treated as data in the zeroth iteration. The error limiting information in the first iteration may be determined (or updated) according to the distribution map of susceptibility property in the zeroth iteration (i.e., the preliminary distribution map of susceptibility property); the distribution map of susceptibility property in the first iteration may be determined (or updated) according to the error limiting information determined in the first iteration. Similarly, the error limiting information in the second iteration may be determined according to the distribution map of susceptibility property determined in the first iteration; the distribution map of susceptibility property in the second iteration may be determined according to the error limiting information updated in the second iteration, and so on. More descriptions regarding the updating of the error limiting information and the distribution map of susceptibility property may be found in, e.g., operations 804, 806 in FIG. 8, and the descriptions thereof.

In some embodiments, after updating the distribution map of susceptibility property and the error limiting information in each iteration, the updating unit 520 may determine whether a termination condition is satisfied. For example, the termination condition may be satisfied when a certain number or count of iterations have been performed in the iterative process. As another example, the termination condition may be satisfied when the difference between the field map corresponding to the updated distribution map of susceptibility property and the preliminary field map (also referred to as a convergence error) is less than a threshold. As a further example, the termination condition may be satisfied when the change of the distribution maps of susceptibility property in two or more successive iterations is less than a threshold. In some embodiments, the threshold may be determined according to error information of an ideal distribution map of susceptibility property of the object. If the convergence error is less than or equal to the threshold, it may be determined that the accuracy of the distribution map of susceptibility property of the object is satisfied, and the iterative process may terminate. More descriptions regarding the determination of whether the termination condition is satisfied may be found in, e.g., operation 808 in FIG. 8, and the descriptions thereof.

In 612, the processing unit 530 may designate the updated distribution map of susceptibility property of the object as a target distribution map of susceptibility property of the object. For example, in response to a determination that the termination condition is satisfied, or the plurality of iterations are completed, the iterative process may terminate and the distribution map of susceptibility property in the current (i.e., last) iteration may be designated as the target distribution map of susceptibility property of the object.

Figure 7:
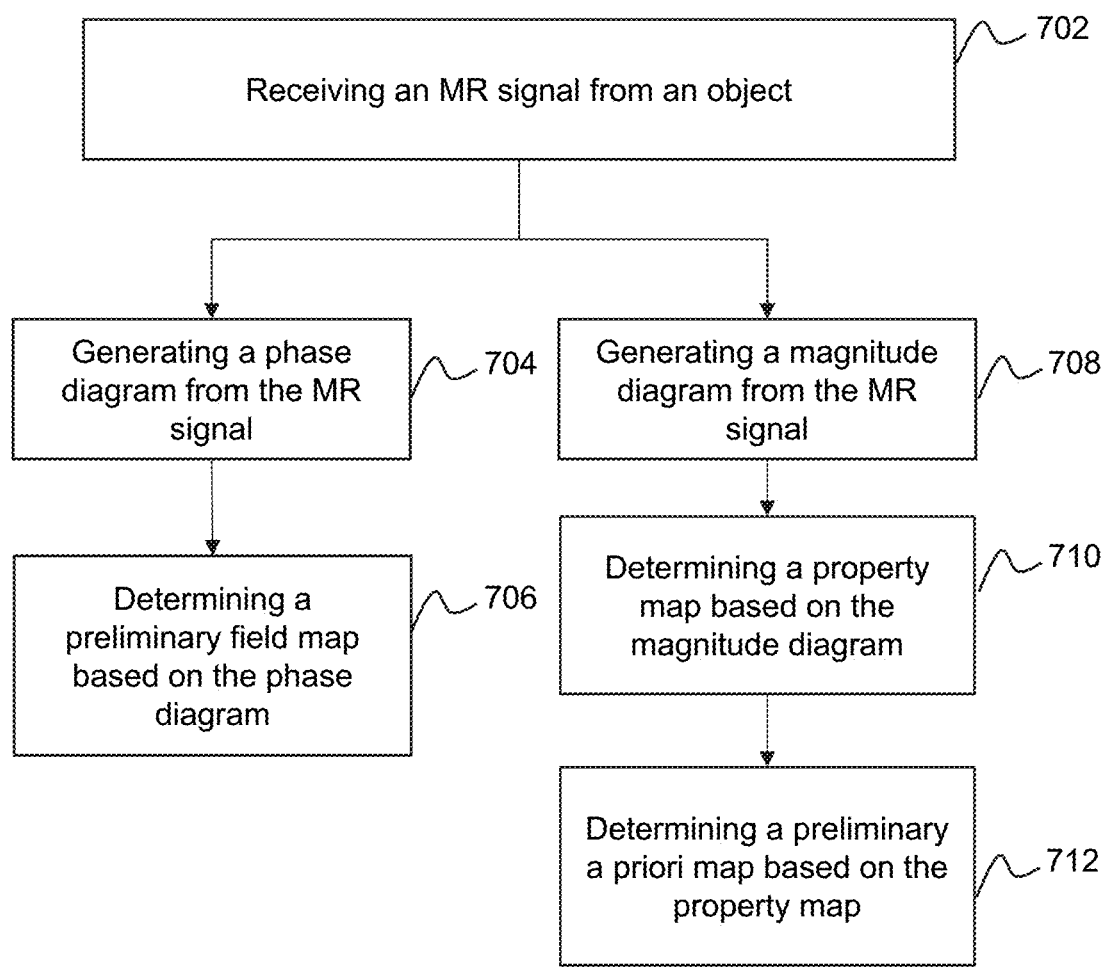
FIG. 7 is a flowchart of an exemplary process for determining a preliminary field map and/or a preliminary a priori map according to some embodiments of the present disclosure.

FIG. 7 is a flowchart of an exemplary process for determining a preliminary field map and/or a preliminary a priori map according to some embodiments of the present disclosure. The process 700 may be executed by the processing device 140. For example, the process 700 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 700. In some embodiments, operations 604 and 606 in FIG. 6 may be performed according to at least a portion of the process 700.

In 702, the acquisition unit 510 may receive an MR signal from an object. In some embodiments, the object or a region of interest (ROI, also referred to as a target site) of the object may be excited by an RF signal. When the object or an ROI of the object relaxes, a spin signal or spin echo may be generated (and/or emitted) by the object (or the ROI of the object) and/or received by the imaging system 100. The spin signal may be phase encoded to form a magnetic resonance (MR) signal. In some embodiments, the MR signal received may be a complex signal including a real part and an imaginary part.

In 704, the processing unit 530 may generate a phase diagram from the MR signal. In some embodiments, the phase diagram may be obtained by performing an inverse tangent function on the ratio between the real part and the imaginary part.

In 706, the processing unit 530 may determine a preliminary field map based on the phase diagram. In some embodiments, the preliminary field map b(r) may be determined based on the phase diagram, as illustrated by Formula (2):

$$\phi(r) = \phi_0(r) + \gamma B_0 b(r) TE, \quad (2)$$

where ø(r) denotes the phase diagram, $Ø_0(r)$ denotes the initial phase that relates to the structure of the RF signal transmitting coil(s), γ denotes the gyromagnetic ratio that is constant for the same nuclei and field strength (e.g., the gyromagnetic ratio for a hydrogen proton in a 3 Tesla magnetic field is 127.8 MHz), $B_0$ denotes the strength of the main magnetic field, b(r) denotes the field map (e.g., the preliminary field map), and TE denotes the echo time of the spin echo.

In 708, the processing unit 530 may generate a magnitude diagram from the MR signal. In some embodiments, the magnitude diagram may be obtained by taking a square root of the sum of squares of the real part and squares of the imaginary part of the MR signal. For example, for an MR signal S=a+i*b, the amplitude of the MR signal $M=(a^2+b^2)^{0.5}$.

In 710, the processing unit 530 may determine a feature map based on the magnitude diagram. In some embodiments, properties of the magnitude diagram may be extracted to generate the feature map. The properties may include the gradient property along one or more reference directions (e.g., the X direction, the Y direction, and/or the Z direction) of the magnitude diagram. The feature map may also be referred to as a gradient map. For example, the magnitude diagram may include a plurality of pixels, and each pixel of the magnitude diagram may have a pixel value. The feature map may include a plurality of pixels having a one-to-one correspondence with the plurality of pixels of the magnitude diagram. For each of the plurality of pixels in the feature map, the value of the pixel may be determined as an evaluation value between a pixel value of a first pixel and a pixel value of a neighboring pixel adjacent to the first pixel of the magnitude diagram along a certain reference direction. As used herein, two pixels are referred to as neighboring pixels if the two pixels are right next to each other and not spaced apart by another pixel along a certain direction.

In 712, the processing unit 530 may determine a preliminary a priori map based on the feature map. In some embodiments, the feature map obtained in the operation 710 may be directly designated as the preliminary a priori map. Alternatively, in order to emphasize the boundary information in the feature map, an image binarization may be performed on the feature map to generate the preliminary a priori map. For instance, the image binarization may include resetting pixel values of pixels to zero or one by comparing the pixel values with a threshold according to a rule. In some embodiments, if the pixel value of a pixel is lower than a threshold, the pixel value of the pixel may be reset to zero; if the pixel value of a pixel is higher than the threshold, the pixel value may be reset to one. If the pixel value of a pixel is equal to the threshold, the pixel value of the pixel may be reset to zero or one according to the rule. The rule may be set by the imaging system 100 according to a default setting thereof, or provided by a user, etc. In some embodiments, the threshold may be a relatively low number (e.g., slightly lower than the gradient value of the pixels along inner boundaries) so that both an outer boundary (e.g., a boundary between the object and air) and an inner boundary (e.g., a boundary between different types of tissue inside the object) may be retained. Alternatively, the threshold may be a relatively high number (e.g., higher than the gradient value of the pixels along an inner boundary but lower than the gradient value of the pixels along an outer boundary) so that only the outer boundary is retained.

In some embodiments, 708, 710 and 712 may be performed or omitted. If 708, 710 and 712 are performed, the processing result may correspond to the panel 1302; if 708, 710 and 712 are omitted, the processing result may correspond to the panel 1304.

Figure 8:
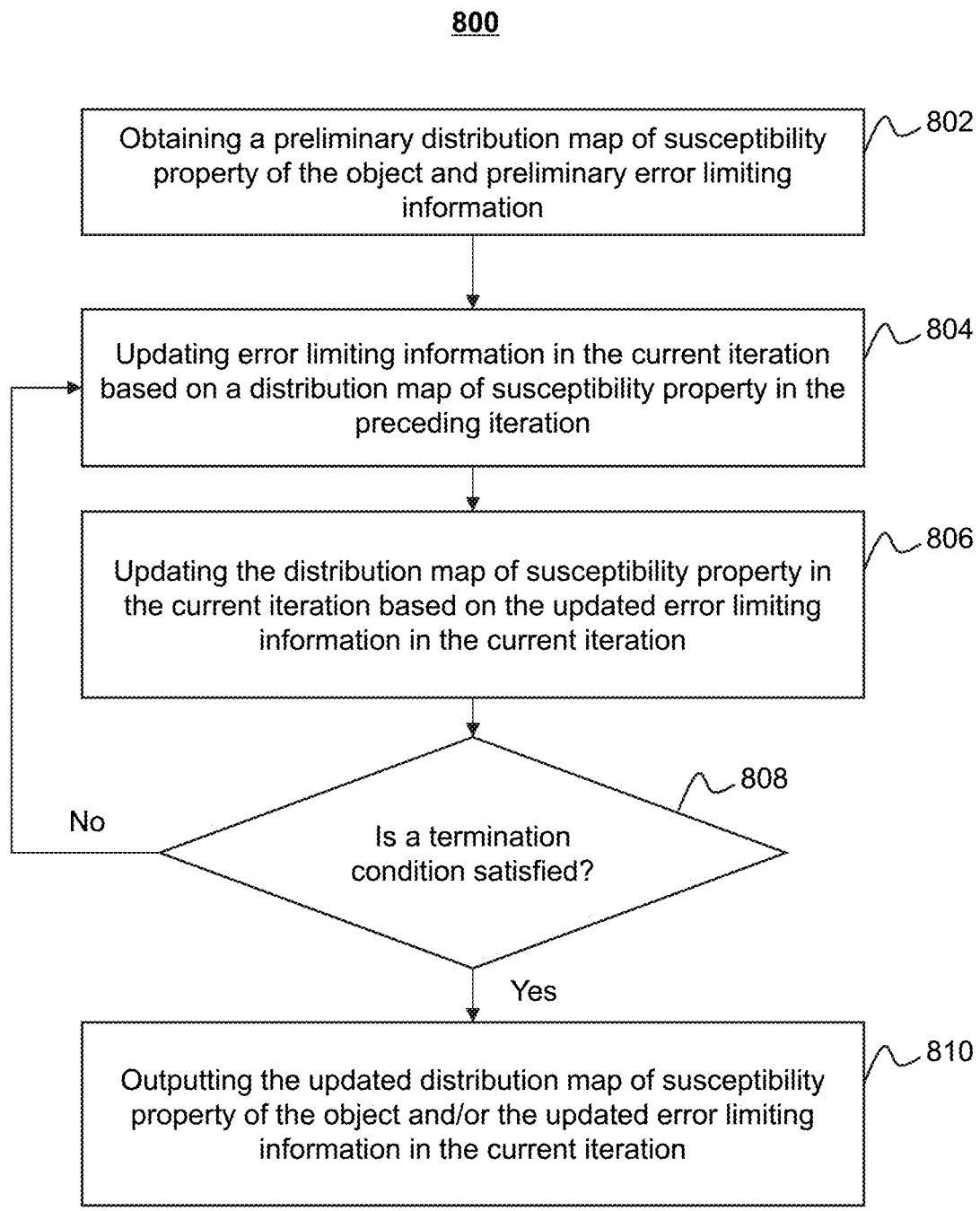
FIG. 8 is a flowchart of an exemplary process for iteratively updating the distribution map of susceptibility property and/or error limiting information according to some embodiments of the present disclosure.

FIG. 8 is a flowchart of an exemplary process for iteratively updating the distribution map of susceptibility property and/or error limiting information according to some embodiments of the present disclosure. The process 800 may be executed by the processing device 140. For example, the process 800 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 800. In some embodiments, operation 610 in FIG. 6 may be performed according to at least a portion of the process 800.

In 802, the acquisition unit 510 may obtain a preliminary distribution map of susceptibility property of the object and preliminary error limiting information (e.g., the preliminary a priori information and/or the preliminary artifact estimation information). In some embodiments, the preliminary distribution map of susceptibility property of the object may be generated by an operation described in operation 608 and the preliminary error limiting information may be generated by an operation described in operation 712. Merely by way of example, the preliminary distribution map of susceptibility property and the preliminary error limiting information may be treated as data in the zeroth iteration.

In 804, the updating unit 520 may update error limiting information in the current iteration based on a distribution map of susceptibility property in the preceding iteration. For example, in the first iteration, the updating unit 520 may update error limiting information in the first iteration based on a distribution map of susceptibility property in the zeroth iteration (i.e., the preliminary distribution map of susceptibility property). Similarly, the error limiting information in the second iteration may be determined according to the distribution map of susceptibility property determined in the first iteration.

Figure 9:
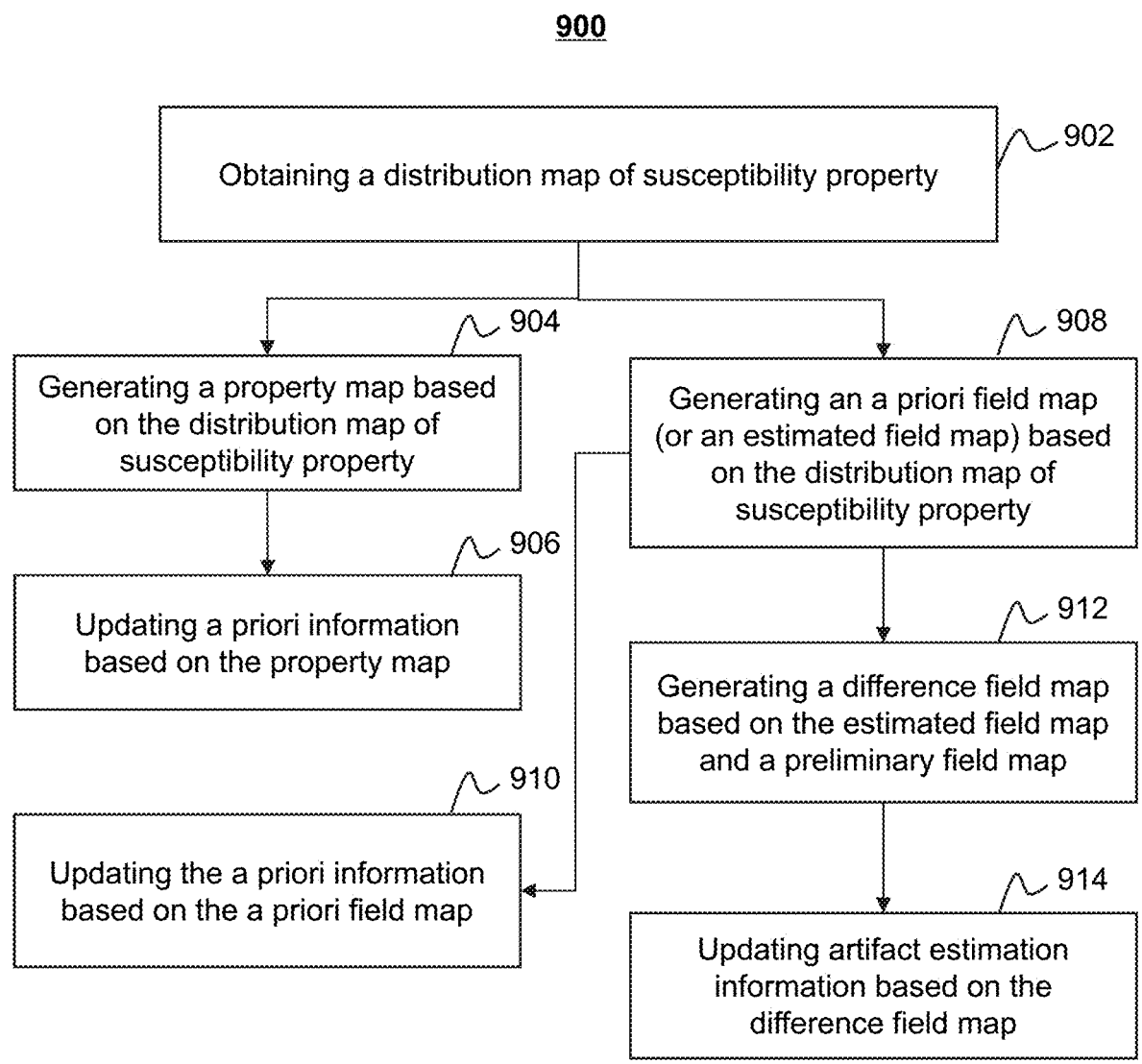
FIG. 9 is a flowchart of an exemplary process for updating the error limiting information according to some embodiments of the present disclosure.

In a case that the error limiting information includes the a priori information (or the a priori map), more descriptions regarding the updating of the error limiting information may be found in, e.g., operations 904 and 906, and operations 908 and 910 in FIG. 9 and the descriptions thereof (showing two different ways of updating the a priori information based on the distribution map of susceptibility property). In a case that the error limiting information include the artifact estimation information (or an artifact estimation map, a streaking artifact estimation map), more descriptions regarding the updating of the error limiting information may be found in, e.g., operations 908, 912, and 914. In a case that the error limiting information includes both the a priori information and the artifact estimation information, the updating unit 520 may update the a priori information and the artifact estimation information separately in any order or simultaneously.

In 806, the updating unit 520 may update the distribution map of susceptibility property in the current iteration based on the updated error limiting information determined in the current iteration. For example, the distribution map of susceptibility property in the first iteration may be determined (or updated) according to the error limiting information determined in the first iteration. Similarly, the distribution map of susceptibility property in the second iteration may be determined according to the error limiting information updated in the second iteration, and so on. In some embodiments, the distribution map of susceptibility property may be updated based on the error limiting information using Formula (1).

As already discussed, Formula (1) describes an optimization process, e.g., seeking for a value $\chi$ to make the value of Formula (1) minimum or less than a threshold. In each of the plurality of iterations, Formula (1) may be used to determine a distribution map of susceptibility property $\chi$ based on an updated difference map $\Delta\phi$ (related to artifact estimation information) and an updated property mask P (related to the a priori information). The updated distribution map of susceptibility property $\chi$ may then be used to update the difference map $\Delta\phi$ and the property mask P. Merely by way of example, Formula (1) may be solved by any kinds of numerical optimization algorithm including, e.g., a conjugate gradient, a preconditioned conjugate gradient, quadratic minimization, split-Bregman, or the like, or any combination thereof.

It should be noted that Formula (1) includes both the a priori information and the artifact estimation information. In a case that the error limiting information only includes the a priori information, the third part $\beta\|F^{-1}D'F\Delta\phi\|_2^2$ in Formula (1) may be omitted and Formula (1) may be reduced to:

$$\mathrm{argmin}_\chi \|F^{-1}DF\chi-\phi\|_2^2+\alpha\|P\nabla\chi\|_1. \qquad (3)$$

In a case that the error limiting information only includes the artifact estimation information, the term $\alpha\|P\nabla\chi\|_1$ in Formula (1) may be omitted and Formula (1) may be reduced to:

$$\mathrm{argmin}_\chi \|F^{-1}DF\chi-\phi\|_2^2+\beta\|F^{-1}D'F\Delta\phi\|_2^2. \qquad (4)$$

Figure 10:
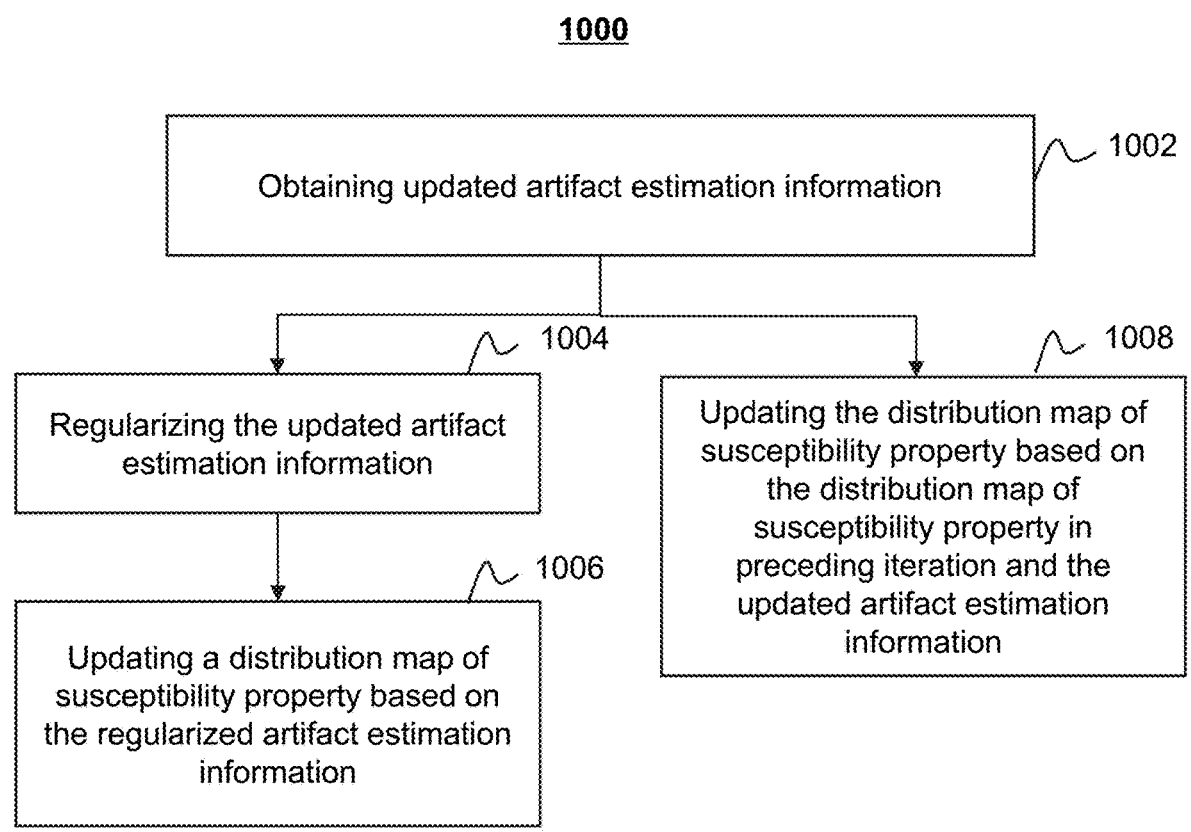
FIG. 10 is a flowchart of an exemplary process for updating the distribution map of susceptibility property according to some embodiments of the present disclosure.

More descriptions regarding the updating of distribution map of susceptibility property based on the artifact estimation information may be found in, e.g., FIG. 10 and the descriptions thereof.

In 808, the updating unit 520 may determine whether a termination condition is satisfied. For example, the termination condition may be satisfied when a certain number of count of iterations have been performed in the iterative process. As another example, the termination condition may be satisfied when the difference between field map related to the updated distribution map of susceptibility property and the preliminary field map (also referred to as a convergence error) is less than a threshold. As a further example, the termination condition may be satisfied when the change of distribution maps of susceptibility property in two or more successive iterations is less than a threshold. More descriptions regarding the determination as to whether the difference between field map related to the updated distribution map of susceptibility property and the preliminary field map is less than a threshold may be found in, e.g., FIG. 11 and the descriptions thereof. In response to a determination that the termination condition is not satisfied, the process 800 may return to operation 804, and the updating unit 520 may perform a new iteration of updating the error limiting information and the distribution map of susceptibility property in 804 and 806, respectively. In response to a determination that the termination condition is satisfied, the process 800 may proceed to operation 810.

In 810, the processing unit 530 may output the updated distribution map of susceptibility property of the object and/or the updated error limiting information in the current iteration. The outputted distribution map of susceptibility property of the object may be designated as a target distribution map of susceptibility property of the object.

In some embodiments, the process 800 optimizes the susceptibility distribution map through the iterative process. In each of the iterations in the iterative process, the a priori information and/or the artifact estimation information are dynamically updated so that the a priori information and/or the artifact estimation information gradually approach the true value, hence gradually reducing the convergence error (e.g., the evaluation value between the field map corresponding to the magnetic susceptibility map and the preliminary field map), and gradually improving the accuracy of the distribution map of susceptibility property of the object.

FIG. 9 is a flowchart of an exemplary process for updating the error limiting information according to some embodiments of the present disclosure. The process 900 may be executed by the processing device 140. For example, the process 900 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 900. In some embodiments, operation 804 in FIG. 8 may be performed according to at least a portion of the process 900.

In 902, the acquisition unit 510 may obtain a distribution map of susceptibility property. In some embodiments, the distribution map of susceptibility property may be a preliminary distribution map of susceptibility property of the object or an updated distribution map of susceptibility property determined in a preceding iteration. The distribution map of susceptibility property determined during iterations may be updated based on operation 806.

In 904, the processing unit 530 may generate a feature map based on the distribution map of susceptibility property. For example, the feature map may be determined based on the distribution map of susceptibility property of the object updated in the preceding iteration. As another example, the feature map may be determined based on the distribution map of susceptibility property in the preceding iteration and at least one of the magnitude diagram, the phase diagram, the susceptibility weighted imaging (SWI) map, or the R2* (T2*) map. In some embodiments, properties of the distribution map of susceptibility property may be extracted to generate the feature map. The properties may include the gradient property along one or more reference directions (e.g., the X direction, the Y direction, and/or the Z direction, etc.) of the distribution map of susceptibility property. The feature map may also be referred to as a gradient map. The distribution map of susceptibility property of the object (e.g., updated in the current iteration) may include a plurality of pixels, and each pixel of the distribution map of susceptibility property of the object (e.g., updated in the current iteration) may have a pixel value. The feature map may include a plurality of pixels having a one-to-one correspondence with the plurality of pixels of the distribution map of susceptibility property. For each of the plurality of pixels in the feature map, a evaluation value between a pixel value of a first pixel and a pixel value of a neighboring pixel adjacent to the first pixel along a certain reference direction in a preceding iteration may be determined as a value of a pixel in the feature map of the current iteration that corresponds to the first pixel in the distribution map of susceptibility property of the object.

In 906, the updating unit 520 may update a priori information based on the feature map. The a priori information may provide features on the spatial distribution of susceptibility of the object, such as the continuity of distribution within the same tissue, a boundary between different tissues, etc. For example, the a priori information may include spatial smoothness of the susceptibility distribution of the object, a spatial gradient of the susceptibility distribution of the object, edge information of the susceptibility distribution of the object, a weighted property mask, or the like, or any combination thereof, corresponding to the target site of the object. In some embodiments, the updating unit 520 may generate a weighted property mask based on the feature map and the weighted property mask may be designated as the a priori information of the current iteration. The property mask may be an image including a plurality of pixels whose pixel values are, e.g., zeros and ones. For instance, values of pixels in a smooth region (e.g., a region inside or outside a type of tissue of the object that has a relatively low gradient variance) may be zero, while values of pixels near a boundary having a relatively high gradient variance may be one. In some embodiments, the values of pixels may be any value between zero and one. For example, the above-mentioned pixels inside or outside a type of tissue with a low gradient variance may be any number between zero and one (e.g., 0.01, 0.1, 0.3) and the above-mentioned pixels near a boundary may be any number between zero and one (e.g., 0.99, 0.9, 0.7).

The a priori information may be dynamically generated and/or updated based on the intermediate distribution map of susceptibility property obtained during each iteration for obtaining the target distribution map of susceptibility property. The updated a priori information may be applied to the next iteration. In this way, the a priori information may gradually approach the spatial features of the ideal distribution map of susceptibility property, and the iterative convergence rate of the optimization algorithm may also be increased. Furthermore, the accuracy of the results may be improved.

In 908, the processing unit 530 may generate an a priori field map based on the distribution map of susceptibility property. In some embodiments, the a priori field map may be obtained by performing a forward magnetic model function (e.g., using a forward dipole kernel in the forward magnetic model function) on the distribution map of susceptibility property in a preceding iteration. In some embodiments, performing a forward magnetic model function on the distribution map of susceptibility property may also be referred to as performing a forward dipole kernel function on the distribution map of susceptibility property. In some embodiments, the distribution map of susceptibility property in the current iteration may be obtained by performing an inverse magnetic model function (e.g., using an inverse dipole kernel in the inverse magnetic model function) on the a priori field map in the current iteration. In some embodiments, performing an inverse magnetic model function on the a priori field map may also be referred to as performing an inverse dipole kernel function on the a priori field map. The "a priori field map" may also be referred to as the "estimated field map" as in the description of operations 912 and 914. It should be noted that the a priori field map and the estimated field map are two different names to refer to the same thing and they are used interchangeably in the present disclosure.

In some embodiments, the forward magnetic model function may be expressed as:

$$B(r)=B_0 \cdot FT^{-1}\{g(k)\cdot \chi(k)\}. \quad (5)$$

The forward dipole kernel g(k) may be expressed as:

$$g(k) = \begin{cases} \dfrac{1}{3} - \dfrac{k_z^2}{k_x^2+k_y^2+k_z^2}, & k \neq 0 \\ 0, & k = 0 \end{cases}. \quad (6)$$

The inverse magnetic model function may be expressed as:

$$(r)=FT^{-1}\{g^{-1}(k)\cdot FT[\Delta B(r)]\}/B_0, \quad (7)$$

and the inverse dipole kernel $g^{-1}(k)$ may be expressed as:

$$g^{-1}(k) = \begin{cases} 3 \cdot \dfrac{k_x^2+k_y^2+k_z^2}{k_x^2+k_y^2-2k_z^2}, & k \neq 0 \\ 0, & k = 0 \end{cases}, \quad (8)$$

where $\Delta B(r)$ denotes the field map; $\Delta\chi(r)$ denotes the distribution map of susceptibility property; FT and $FT^{-1}$ denotes Fourier transform matrices and inverse Fourier transform matrices, respectively; $\chi$ denotes the magnetic susceptibility distribution; k denotes a Fourier domain coordinate vector; $k_x$ denotes the coordinate in the X direction, $k_y$ denotes the coordinate in the Y direction, $k_z$ denotes the coordinate in the Z direction; r denotes the coordinate vector in the space domain; $B_0$ denotes the external magnetic field; and g and $g^{-1}$ denote the forward magnetic dipole kernel transformation matrix and the inverse magnetic dipole kernel transformation matrix, respectively.

In 910, the updating unit 520 may update the a priori information based on the a priori field map. In some embodiments, the a priori field map may be used as the a priori information in the current iteration.

In 912, the processing unit 530 may generate a difference field map based on the estimated field map and a preliminary field map. Merely by way of example, the pixel value of each pixel in the difference field map may be calculated as the evaluation value between the pixel value of a pixel of the preliminary field map and the pixel value of the corresponding pixel of the estimated field map.

In 914, the updating unit 520 may update artifact estimation information based on the difference field map. In some embodiments, the artifact estimation information may be determined based on the difference field map. For example, the forward dipole kernel D or a partial forward dipole kernel D' may be obtained. The artifact estimation information may be determined based on the forward dipole kernel D (or the partial forward dipole kernel D') and the difference field map as illustrated in the third part of Formula (1). The remnant radiation streaking artifacts may be dynamically estimated during the iterative process of the distribution map of susceptibility property, and may be uses as a regularization term in the iterative process. The operation may reduce the intensity of remnant radiation streaking artifacts to a negligible level without affecting the results of other regularization terms, thereby reducing the artifacts and ensuring the accuracy of the calculation results.

It should be noted that the above description of process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, if the error limiting information only includes the a priori information, operations 912 and 914 may be omitted. As another example, if the error limiting information only includes the artifact estimation information, operations 904, 906, and 910 may be omitted. As a further example, operations 904 and 906 provide a first technique for updating the a priori information, operations 908 and 910 provide a second technique for updating the a priori information, and the operations 904 and 906 and the operations 908 and 910 may be performed alternatively.

FIG. 10 is a flowchart of an exemplary process for updating the distribution map of susceptibility property according to some embodiments of the present disclosure. The process 1000 may be executed by the processing device 140. For example, the process 1000 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 1000. In some embodiments, if the error limiting information includes the artifact estimation information, operation 806 in FIG. 8 may be performed according to at least a portion of the process 1000.

In 1002, the acquisition unit 510 may obtain updated artifact estimation information. For example, the artifact estimation information may be updated based on the distribution map of susceptibility property and the preliminary field map in operations 908, 912 and 914.

In 1004, the processing unit 530 may regularize the updated artifact estimation information. The regularization of the updated artifact estimation information may include introducing additional information in order to solve an ill-posed problem (e.g., the singularity values in the inverse dipole kernel). For example, the artifact estimation information $\|F^{-1}D'F\Delta\phi\|_2^2$ in Formula (1) is regularized by a scaling factor $\beta$ that adjusts the weighting of the remnant streaking artifact regularization term.

In 1006, the updating unit 520 may update a distribution map of susceptibility property based on the regularized artifact estimation information. For example, the distribution map of susceptibility property may be updated based on the regularized artifact estimation information $\beta\|F^{-1}D'F\Delta\phi\|_2^2$ and Formula (1) (or Formula (4)).

In 1008, the updating unit 520 may update the distribution map of susceptibility property based on the distribution map of susceptibility property determined in the preceding iteration and the updated artifact estimation information determined in the current iteration. For example, the distribution map of susceptibility property in the current iteration may be generated by subtracting the updated artifact estimation information determined in the current iteration from the distribution map of susceptibility property in the preceding iteration.

It should be noted that the above description of process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1004 and 1006 provide a first technique for updating the distribution map of susceptibility property based on the updated artifact estimation information, operation 1008 provide a second technique for updating the distribution map of susceptibility property based on the updated artifact estimation information, and the operations 1004 and 1006 and the operation 1008 may be performed alternatively.

Figure 11:
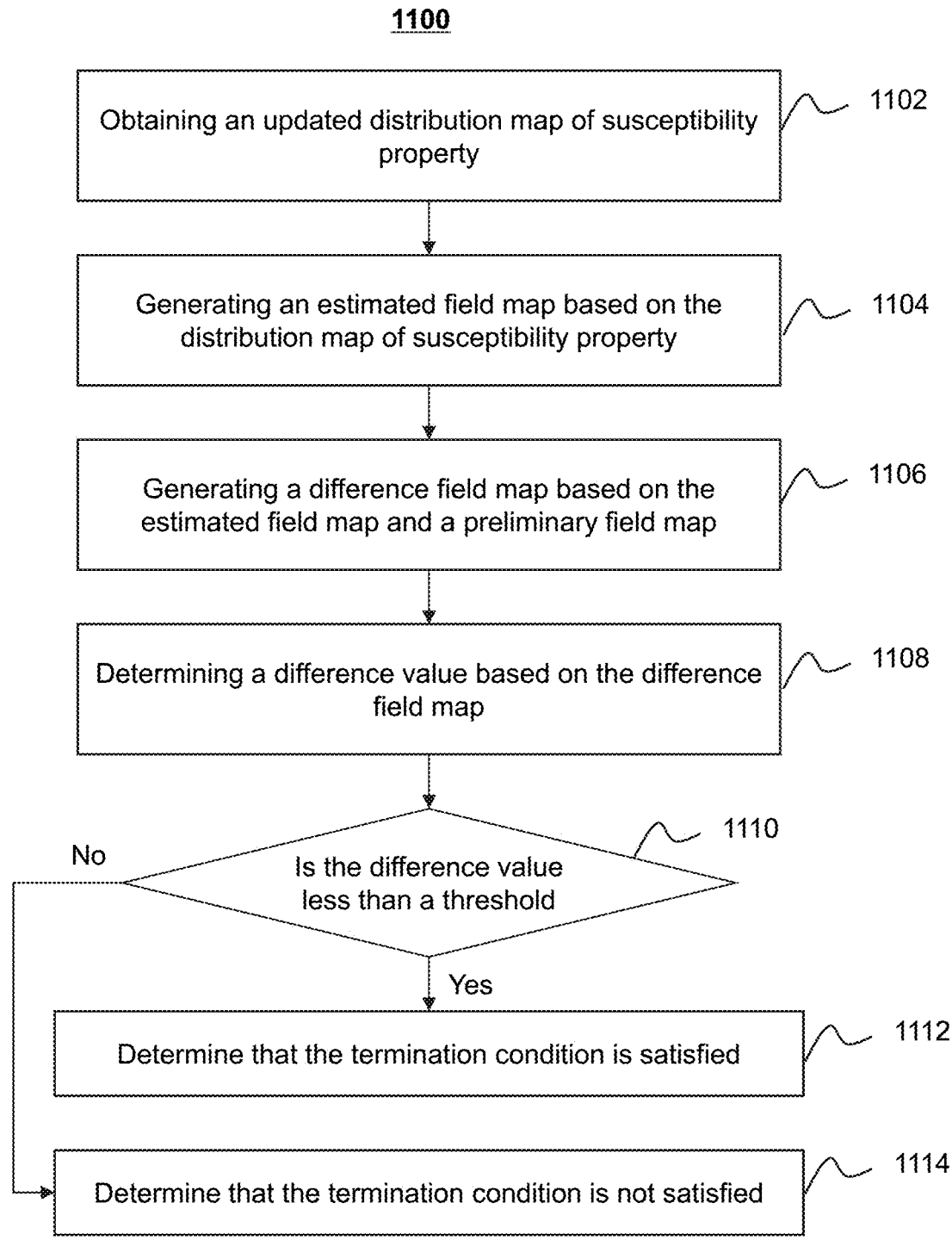
FIG. 11 is a flowchart of an exemplary process for determining whether a termination condition relating to the iteration process is satisfied according to some embodiments of the present disclosure.

FIG. 11 is a flowchart of an exemplary process for determining whether a termination condition relating to the iteration process is satisfied according to some embodiments of the present disclosure. The process 1100 may be executed by the processing device 140. For example, the process 1100 may be implemented as a set of instructions (e.g., an application) stored in the storage, e.g., ROM 230, RAM 240, the storage device 150, the storage 390, a storage device external to and accessible by the imaging system 100. The processing device 140, the CPU 220, the CPU 340, the processing module 440, and/or the processing unit 530 may execute the set of instructions, and when executing the instructions, it may be configured to perform the process 1100. In some embodiments, operation 808 in FIG. 8 may be performed according to the process 1100.

In 1102, the acquisition unit 510 may obtain an updated distribution map of susceptibility property. The distribution map of susceptibility property may be updated as described in operation 806.

In 1104, the processing unit 530 may generate an estimated field map (also referred to as an a priori field map) based on the distribution map of susceptibility property. In some embodiments, the estimated field map may be generated in the current iteration by performing a partial forward dipole kernel function on the updated distribution map of susceptibility property of the object in the current iteration. Similar to operation 908, a forward dipole kernel function may be performed on the distribution map of susceptibility property to generate the estimated field map.

In 1106, the processing unit 530 may generate a difference field map based on the estimated field map and a preliminary field map. Similar to operation 912, the value of each pixel in the difference field map may be determined based on a difference between the value of a pixel in the estimated field map and the value of the corresponding pixel in the preliminary field map. As used herein, two pixels in two different maps or images (e.g., a pixel in an estimated field map and a pixel in a preliminary field map) are considered corresponding to each other if the two pixels correspond to a same physical point in an object or in the imaging system 100.

In 1108, the processing unit 530 may determine an evaluation value (also referred to as a convergence error) based on the difference field map. The evaluation value may represent the condition or the evaluation associated with the difference field map. For example, the evaluation value may be the value of the L1 norm, L2 norm (referred in 608) or a total variance. In some embodiments, the value of L2 norm may be designated as the evaluation value. The evaluation value may be expressed as the square root of the sum of squares of values of all the pixels in the difference field map. For example, the evaluation value may be expressed as:

$$\text{Evaluation value} = \sqrt{\sum_{i=1:X; j=1:Y; k=1:Z} (\text{values of pixels } (x_i, y_j, z_k))^2}, \quad (9)$$

wherein X denotes the size of the difference field map along the X axis; Y denotes the size of the difference field map along the Y axis; and Z denotes the size of the difference field map along the Z axis.

In 1110, the processing unit 530 may determine whether the evaluation value is less than a threshold. In response to a determination that the evaluation value is less than the threshold, the process 1100 may proceed to operation 1112; in response to a determination that the evaluation value exceeds the threshold, the process 1100 may proceed to operation 1114. If the evaluation value is equal to the threshold, the process 1100 may proceed to operation 1112 or operation 1114 according to a rule. The rule may be set by the imaging system 100 according to a default setting thereof, or provided by a user, etc.

In 1112, the processing unit 530 may determine that the termination condition is satisfied, i.e., the updating of the distribution map of susceptibility property may be completed. In some embodiments, in response to a determination that the termination condition is satisfied, the process 1100 may proceed to operation 810.

In 1114, the processing unit 530 may determine that the termination condition is not satisfied, i.e., the updating of the distribution map of susceptibility property is not completed.

In some embodiments, in response to a determination that the termination condition is not satisfied, the process 1100 may return to operation 804.

Figure 12:
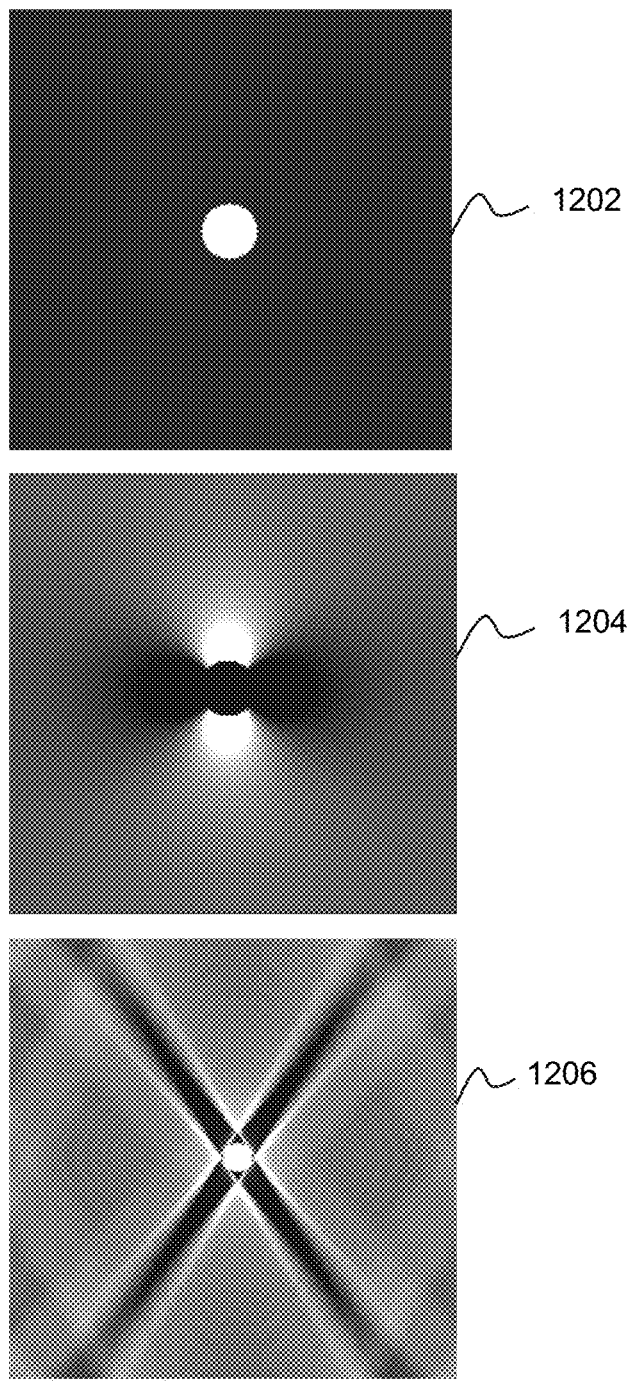
FIG. 12 is a schematic diagram illustrating an exemplary ideal distribution map of susceptibility property, an exemplary field map, and an exemplary reconstructed distribution map of susceptibility property with artifacts according to some embodiments of the present disclosure.

FIG. 12 is a schematic diagram illustrating an exemplary ideal distribution map of susceptibility property, an exemplary field map, and an exemplary reconstructed distribution map of susceptibility property with artifacts according to some embodiments of the present disclosure. In some embodiments, the image 1202 may be an unknown but a target distribution map of susceptibility property of a cylinder. The image 1204 may be an acquired field map of the cylinder in image 1202. The image 1206 may be a distribution map of susceptibility property that is directly reconstructed from the image 1204. It should be noted that the image 1206 contains apparent artifacts. The goal of the techniques disclosed in the present application is to generate the image 1202 based on the image 1204.

EXAMPLES

The following examples are shown for illustration purposes and not intended to limit the scope of the present disclosure.

Figure 13:
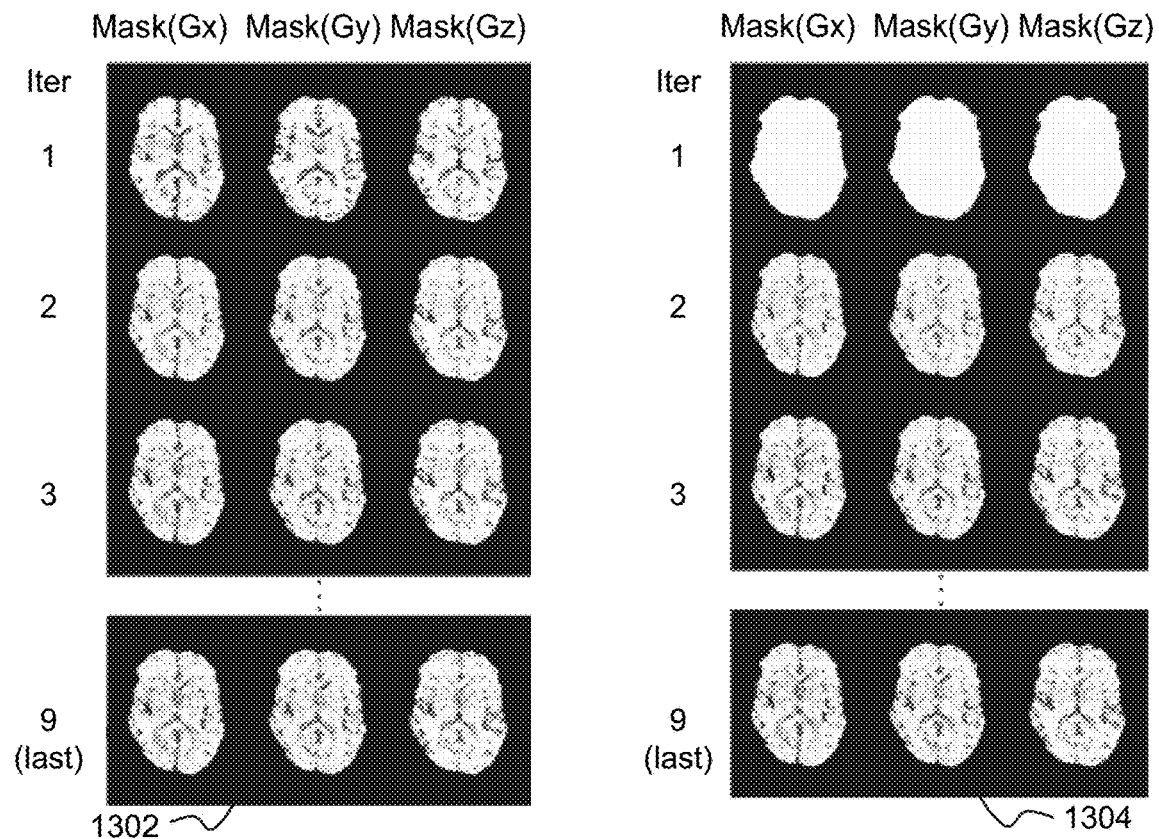
FIG. 13 is a schematic diagram illustrating exemplary schemes of iteratively updating a priori information according to some embodiments of the present disclosure.
Figure 13:
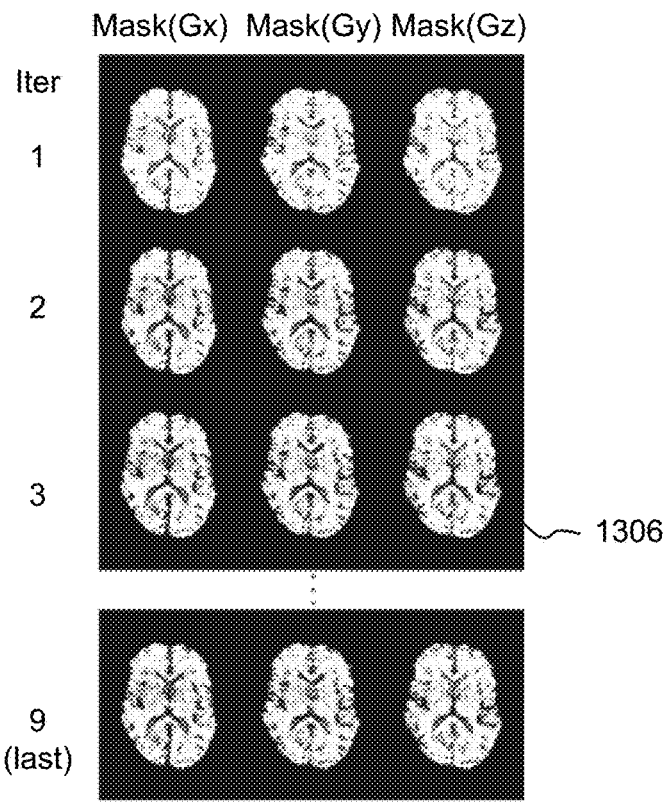

FIG. 13 is a schematic diagram illustrating exemplary schemes of iteratively updating a priori information according to some embodiments of the present disclosure. As shown in FIG. 13, an example of a specific experimental result of iteratively (or dynamically) updating a priori information is shown. The a priori information in this example is a weighted property mask obtained from the spatial gradient features (e.g., the gradient variance) of the image. The image spatial gradient was calculated independently in the three directions of the X direction, the Y direction, and the Z direction as illustrated in FIG. 1, and three corresponding gradient maps Gx, Gy, and Gz were obtained. The gradient maps Gx, Gy, and Gz were extracted as a mask (Gx), a mask (Gy), and a mask (Gz), respectively. In the present example, pixels were set according to a thresholding technique. When the value of a certain pixel in the gradient map(s) exceeded the threshold, the pixel value of pixels in the corresponding weighted property mask was set to 0 (white); otherwise, the pixel value of pixels in the corresponding weighted property mask was set to 1 (black).

Panel 1302 shows mask Gx, mask Gy, and mask Gz determined in the first iteration through the third iteration, and the ninth iteration of the iterative process. The initial weighted property mask (i.e., before the first iteration) was determined based on the magnitude diagram. In each iteration of the iterative process of updating the distribution map of susceptibility property, the weighted property mask was updated based on the distribution map of susceptibility property in the preceding iteration and used for updating the distribution map of susceptibility property in the current iteration. In some embodiments, the panel 1302 may correspond to the processing result when the steps 708, 710 and 712 are performed.

Panel 1304 shows mask Gx, mask Gy, and mask Gz determined in the first iteration through the third iteration, and the ninth iteration of the iterative process. The initial weighted property mask was determined based on a brain mask, e.g., the initial weighted property mask does not contain useful a priori knowledge. In each iteration of the iterative process of updating the distribution map of susceptibility property, the weighted property mask was updated based on the distribution map of susceptibility property in the preceding iteration and used for updating the distribution map of susceptibility property in the current iteration. In some embodiments, the panel 1304 may correspond to the processing result when the steps 708, 710 and 712 are not performed.

Panel 1306 shows mask Gx, mask Gy, and mask Gz determined in the first iteration through the third iteration, and the ninth iteration of the iterative process. The initial weighted property mask was determined based on the magnitude diagram. In each iteration of the iterative process of updating the distribution map of susceptibility property, the weighted property mask was updated based on both the distribution map of susceptibility property in the preceding iteration and the initial weighted property mask (e.g., by a superposition operation). Hence, the difference between panel 1302 and panel 1306 is that the weighted property mask in panel 1306 contains both the spatial a priori information of the intermediate susceptibility map and the spatial a priori information of the magnitude diagram, while the panel 1302 only contains the spatial a priori information of the intermediate susceptibility map.

It should be noted that by combining both the intermediate distribution map of susceptibility property and the initial weighted property mask to dynamically (or iteratively) update the a priori information as shown in panel 1306, a clearer property mask may be obtained. Therefore, a clearer and more accurate distribution map of susceptibility property may be generated based on the clearer property mask. It should be noted that all the techniques disclosed in generating masks illustrated in panels 1302, 1304, and 1306 may be implemented by the imaging system 100 and are within the protection scope of the present disclosure.

Figure 14:
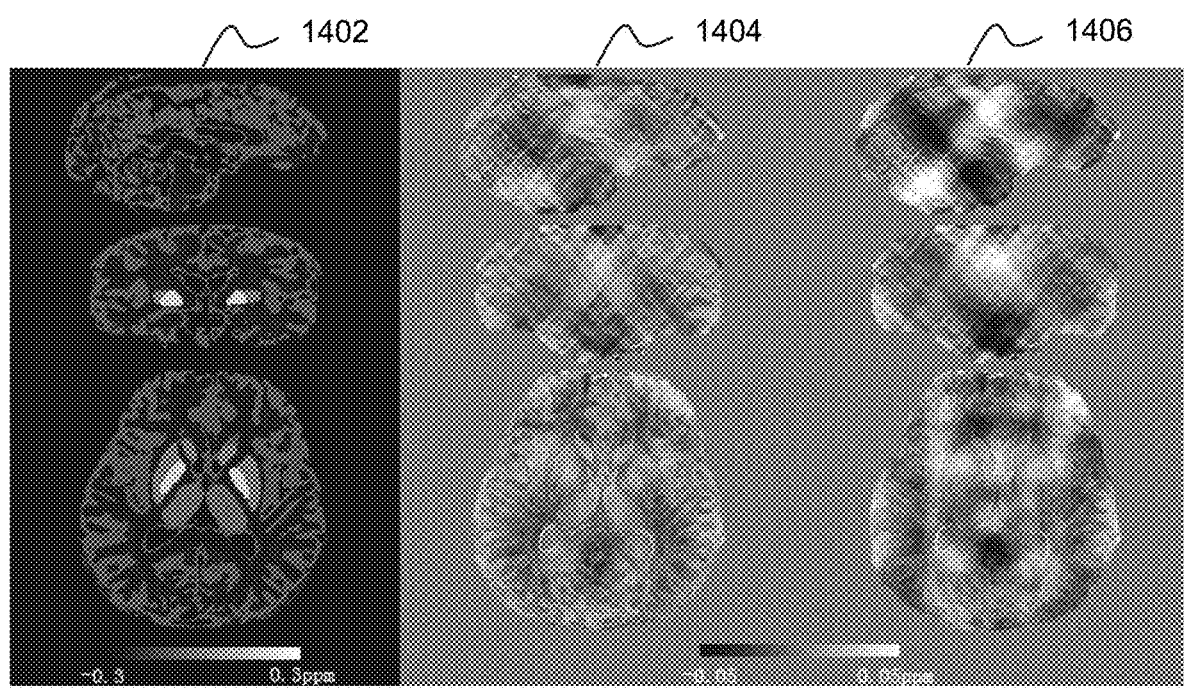
FIG. 14 is a schematic diagram illustrating exemplary computer simulated demonstrations of artifact of various amount in the distribution map of susceptibility property according to some embodiments of the present disclosure.

FIG. 14 is a schematic diagram illustrating exemplary computer simulated demonstrations of artifact of various amount in the distribution map of susceptibility property according to some embodiments of the present disclosure. The left column 1402 is an ideal distribution map of susceptibility property generated by computer simulation. The middle column 1404 is a difference map between the ideal distribution map of susceptibility property in the left column 1402 and the target distribution map of susceptibility property generated according to the processes disclosed in, e.g., FIGS. 6-11 of the present disclosure (e.g., dynamically updating the a priori information, the remnant streaking artifact estimation information and the distribution map of susceptibility property). The right column 1406 is a difference map between the ideal distribution map of susceptibility property in the left column 1402 and the distribution map of susceptibility property generated by the conventional QSM technique. The gray levels of the pixels of the ideal distribution map of susceptibility property in the left column 1402 may be in a range of −0.3~0.3 part per million (ppm), in which the highest gray level may be 0.3 ppm or even higher, while the lowest gray level may be −0.3 ppm or even lower. Each of the pixels of the difference maps in the middle column 1404 and the right column 1406 is presented in difference in brightness indicating its value. For example, the darkest pixel in the difference maps may correspond to a value of −0.05 part per million (ppm), and the brightest pixel in the difference maps may correspond to a value of 0.05 ppm. It can be seen from FIG. 14 that the values of pixels of the difference map in the middle column 1404 are much closer to zero (bright pixels are less bright and dark pixels are less dark) than the difference map in the right column 1406. This may indicate that the distribution map of susceptibility property determined by the present technique described in the present disclosure is more accurate with less convergence error than the conventional QSM technique.

Figure 15:
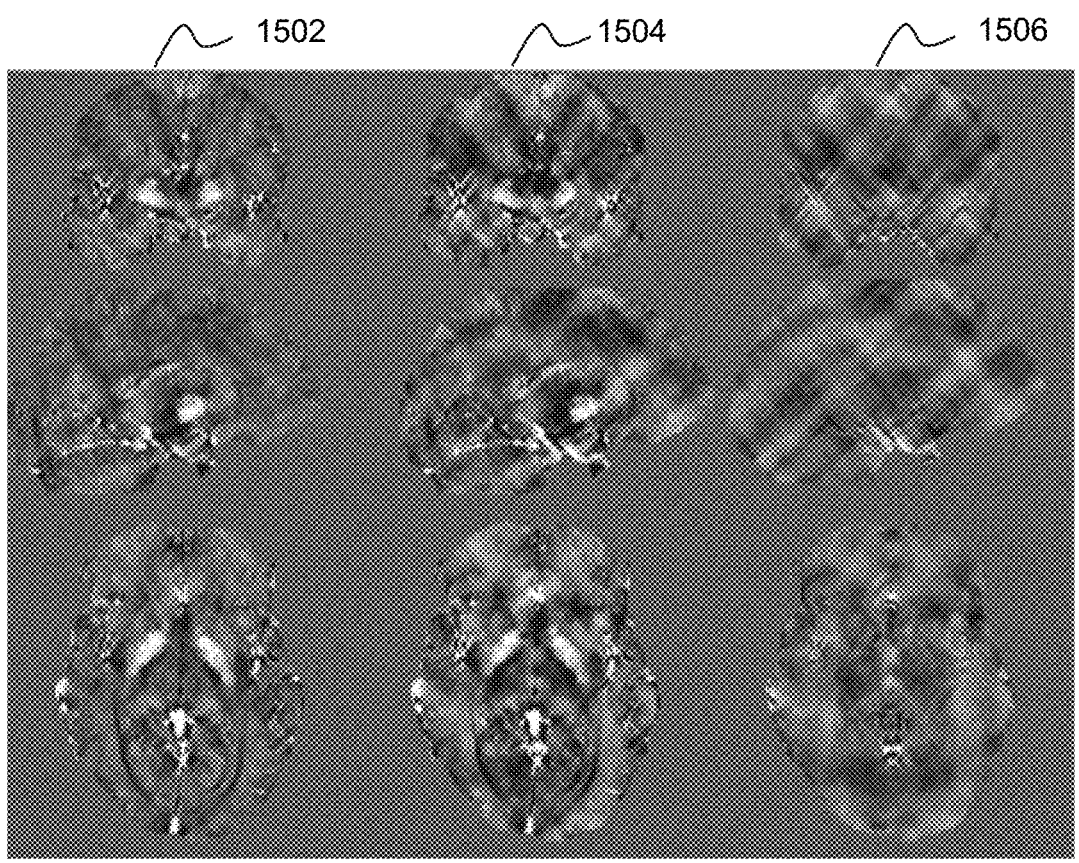
FIG. 15 is a schematic diagram illustrating exemplary human brain images demonstrating artifacts of various amount in the distribution maps of susceptibility property according to some embodiments of the present disclosure.

FIG. 15 is a schematic diagram illustrating exemplary human brain images demonstrating artifacts of various amount in the distribution maps of susceptibility property according to some embodiments of the present disclosure. Column 1502 illustrates three distribution maps of susceptibility property generated according to the technique disclosed in, e.g., FIGS. 6-11 of the present disclosure (e.g., dynamically updating the a priori information, the remnant streaking artifact estimation information and the distribution map of susceptibility property). Column 1504 illustrates three distribution maps of susceptibility property generated according to the conventional QSM technique. Column 1506 illustrates three difference maps between column 1502 and column 1504. Each row of columns 1502-1506 illustrates a three-dimensional human brain image obtained based on the same scan data. As shown in FIG. 15, the images in column 1502 have a relatively low level of streaking artifacts, indicating that the technique described in the present disclosure is effective in eliminating or suppressing artifacts compared with the conventional QSM technique.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a specific feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the specific features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method implemented on a computing device having at least one storage device storing a set of instructions for determining a distribution map of susceptibility property of an object and at least one processor in communication with the at least one storage device, the method comprising:
obtaining a phase diagram corresponding to a magnetic resonance (MR) signal of the object;
determining a preliminary field map based on the phase diagram;
obtaining preliminary error limiting information associated with the preliminary field map;
determining, based on the preliminary field map and the preliminary error limiting information, a preliminary distribution map of susceptibility property of the object;
performing an iteration process including at least one iteration, wherein each of the at least one iteration comprises:
updating error limiting information in a current iteration based on a distribution map of susceptibility property of the object updated in a preceding iteration;
updating the distribution map of susceptibility property of the object in the current iteration based on the error limiting information updated in the current iteration; and
performing a comparison based on the updated distribution map in the current iteration and the preliminary field map; and
designating the updated distribution map of susceptibility property of the object as a target distribution map of susceptibility property of the object.

2. The method of claim 1, wherein the performing a comparison based on the updated distribution map in the current iteration and the preliminary field map comprises:
generating an estimated field map based on the updated distribution map of susceptibility property of the object in the current iteration;
comparing the estimated field map with the preliminary field map; and
determining whether the updated distribution map in the current iteration satisfies a condition based on a result of the comparison between the estimated field map and the preliminary field map.

3. The method of claim 2, wherein the comparing the estimated field map with the preliminary field map comprises:
determining a difference field map between the estimated field map and the preliminary field map;
determining an evaluation value based on the difference field map; and
the determining whether the updated distribution map in the current iteration satisfies a condition comprising:
comparing the evaluation value with a threshold.

4. The method of claim 1, wherein the error limiting information comprises an a priori map, and the obtaining preliminary error limiting information comprises:
determining at least one of a magnitude diagram, a phase diagram, a susceptibility weighted imaging (SWI) map, or a R2* (T2*) map based on the MR signal; and
determining a preliminary a priori map based on the at least one of the magnitude diagram, the phase diagram, the susceptibility weighted imaging (SWI) map, or the R2* (T2*) map.

5. The method of claim 1, wherein the error limiting information comprises an a priori map, and the updating error limiting information in a current iteration based on the distribution map of susceptibility property of the object updated in a preceding iteration comprises:
determining a feature map in the current iteration based at least in part on the distribution map of susceptibility property of the object updated in the preceding iteration; and
updating the a priori map based on the feature map.

6. The method of claim 5, wherein
the distribution map of susceptibility property of the object updated in the current iteration includes a plurality of pixels, each pixel of the distribution map of susceptibility property of the object in the current iteration having a pixel value,
the feature map includes a plurality of pixels having a one-to-one correspondence with the plurality of pixels of the distribution map of susceptibility property of the object, and
the determining a feature map in the current iteration based on the distribution map of susceptibility property of the object updated in the preceding iteration comprises:
for each of the plurality of pixels in the feature map, determining an evaluation value between a pixel value of a first pixel and a pixel value of a second pixel adjacent to the first pixel in the distribution map of susceptibility property of the object in the preceding iteration; and
designating the evaluation value as a pixel value of a pixel in the feature map of the current iteration that corresponds to the first pixel in the distribution map of susceptibility property of the object.

7. The method of claim 6, wherein the determining an evaluation value between a pixel value of a first pixel and a pixel value of a second pixel next to the first pixel in the distribution map of susceptibility property of the object in the preceding iteration comprises:
determining the evaluation value between the pixel value of the first pixel and the pixel value of the second pixel next to the first pixel in a reference direction, the reference direction including at least one of an X direction, a Y direction, or a Z direction.

8. The method of claim 1, wherein the error limiting information comprises an a priori map, and the updating error limiting information in a current iteration based on the distribution map of susceptibility property of the object in a preceding iteration comprises:
determining an a priori field map in the current iteration based on the distribution map of susceptibility property of the object in the preceding iteration; and
updating the a priori map in the current iteration based on the a priori field map in the current iteration.

9. The method of claim 8, wherein determining an a priori field map in the current iteration based on the distribution map of susceptibility property of the object in the preceding iteration comprises:
determining the a priori field map in the current iteration by performing a forward dipole kernel function on the distribution map of susceptibility property of the object in the preceding iteration.

10. The method of claim 1, wherein the error limiting information comprises an artifact estimation map, and the updating error limiting information in a current iteration based on the distribution map of susceptibility property of the object in a preceding iteration comprises:
generating an estimated field map in the current iteration based on the updated distribution map of susceptibility property of the object in the current iteration;
determining a difference field map between the estimated field map in the current iteration and the preliminary field map; and
updating the artifact estimation map in the current iteration based on the difference field map.

11. The method of claim 10, wherein generating an estimated field map in the current iteration based on the updated distribution map of susceptibility property of the object in the current iteration comprises:
generating the estimated field map in the current iteration by performing a partial forward dipole kernel function on the updated distribution map of susceptibility property of the object in the current iteration.

12. The method of claim 10, wherein the updating the distribution map of susceptibility property of the object in the current iteration based on the error limiting information updated in the current iteration comprises:
generating the updated distribution map of susceptibility property of the object in the current iteration by subtracting an updated artifact estimation map in the current iteration from the distribution map of susceptibility property of the object in the preceding iteration; or
generating the updated distribution map of susceptibility property of the object in the current iteration by using a regularization term relating to an updated artifact estimation map in the iteration process.

13. The method of claim 1, wherein the error limiting information includes an a priori map and an artifact estimation map, and the updating the distribution map of susceptibility property of the object in the current iteration based on the error limiting information updated in the current iteration comprises:
generating the updated distribution map of susceptibility property of the object in the current iteration based on the a priori map in the current iteration, the artifact estimation map in the current iteration and the preliminary field map.

14. The method of claim 1, wherein the iteration process is performed based on at least one of a conjugate gradient, a preconditioned conjugate gradient, quadratic minimization, or split-Bregman.

15. The method of claim 1, wherein the error limiting information includes an a priori map relating to a spatial smoothness, a spatial gradient, edge information, or a weighted property mask of the distribution map of susceptibility property of the object.

16. A system comprising:
at least one storage including a set of instructions or programs for determining a distribution map of susceptibility property of an object;
at least one processor configured to communicate with the at least one storage, wherein when executing the set of instructions or programs, the at least one processor is directed to perform operations including:
obtaining a phase diagram corresponding to a magnetic resonance (MR) signal of the object;
determining a preliminary field map based on the phase diagram;
obtaining preliminary error limiting information associated with the preliminary field map;
determining, based on the preliminary field map and the preliminary error limiting information, a preliminary distribution map of susceptibility property of the object;
performing an iteration process including at least one iteration, wherein in each of the at least one iteration includes:
updating error limiting information in a current iteration based on a distribution map of susceptibility property of the object updated in a preceding iteration;

updating the distribution map of susceptibility property of the object in the current iteration based on the error limiting information updated in the current iteration; and performing a comparison based on the updated distribution map in the current iteration and the preliminary field map; and designating the updated distribution map of susceptibility property of the object as a target distribution map of susceptibility property of the object.

17. The system of claim 16, wherein to perform a comparison based on the updated distribution map in the current iteration and the preliminary field map, the at least one processor is directed to perform additional operations including:

generating an estimated field map based on the updated distribution map of susceptibility property of the object in the current iteration;

comparing the estimated field map with the preliminary field map; and determining whether the updated distribution map in the current iteration satisfies a condition based on a result of the comparison between the estimated field map and the preliminary field map.

18. The system of claim 16, wherein the error limiting information comprises an a priori map, and to obtain preliminary error limiting information, the at least one processor is directed to perform additional operations including:

determining at least one of a magnitude diagram, a phase diagram, a susceptibility weighted imaging (SWI) map, or a R2* (T2*) map based on the MR signal; and determining a preliminary a priori map based on the at least one of the magnitude diagram, the phase diagram, the susceptibility weighted imaging (SWI) map, or the R2* (T2*) map.

19. The system of claim 16, wherein the error limiting information comprises an artifact estimation map, and to update error limiting information in a current iteration based on the distribution map of susceptibility property of the object in a preceding iteration, the at least one processor is directed to perform additional operations including:

generating an estimated field map in the current iteration based on the updated distribution map of susceptibility property of the object in the current iteration;

determining a difference field map between the estimated field map in the current iteration and the preliminary field map; and updating the artifact estimation map in the current iteration based on the difference field map.

20. A non-transitory computer readable medium comprising executable instructions or programs that, when executed by at least one processor, cause the at least one processor to effectuate a method comprising:

obtaining a phase diagram corresponding to a magnetic resonance (MR) signal of the object;

determining a preliminary field map based on the phase diagram;

obtaining preliminary error limiting information associated with the preliminary field map;

determining, based on the preliminary field map and the preliminary error limiting information, a preliminary distribution map of susceptibility property of the object;

performing an iteration process including at least one iteration, wherein each of the at least one iteration includes:

updating error limiting information in a current iteration based on a distribution map of susceptibility property of the object updated in a preceding iteration;

updating the distribution map of susceptibility property of the object in the current iteration based on the error limiting information updated in the current iteration; and performing a comparison based on the updated distribution map in the current iteration and the preliminary field map; and designating the updated distribution map of susceptibility property of the object as a target distribution map of susceptibility property of the object.

* * * * *